US011056331B2

(12) United States Patent
Stumbo et al.

(10) Patent No.: US 11,056,331 B2
(45) Date of Patent: Jul. 6, 2021

(54) SOURCE-DETECTOR SYNCHRONIZATION IN MULTIPLEXED SECONDARY ION MASS SPECTROMETRY

(71) Applicant: IONpath, Inc., Menlo Park, CA (US)

(72) Inventors: David Stumbo, Pleasanton, CA (US); Sean Bendall, San Mateo, CA (US); Michael Angelo, Menlo Park, CA (US); Stephen Thompson, Gringley on the Hill (GB); Harris Fienberg, Redwood City, CA (US)

(73) Assignee: IONpath, Inc., Menlo Park, CA (US)

( * ) Notice: Subject to any disclaimer, the term of this patent is extended or adjusted under 35 U.S.C. 154(b) by 0 days.

(21) Appl. No.: 16/288,575

(22) Filed: Feb. 28, 2019

(65) Prior Publication Data
US 2019/0267227 A1 Aug. 29, 2019

Related U.S. Application Data

(60) Provisional application No. 62/636,220, filed on Feb. 28, 2018.

(51) Int. Cl.
*H01J 49/00* (2006.01)
*H01J 49/40* (2006.01)
(Continued)

(52) U.S. Cl.
CPC ........ *H01J 49/403* (2013.01); *G01N 33/6848* (2013.01); *H01J 49/0031* (2013.01);
(Continued)

(58) Field of Classification Search
CPC ...... H01J 49/403; H01J 49/142; H01J 49/022; H01J 49/025; H01J 49/0031; G01N 33/6848
(Continued)

(56) References Cited

U.S. PATENT DOCUMENTS

| 3,668,384 A * | 6/1972 | Moorman ............ H01J 49/025 250/287 |
| 7,126,114 B2 * | 10/2006 | Chernushevich ... H01J 49/0031 250/287 |

(Continued)

FOREIGN PATENT DOCUMENTS

| EP | 1 990 827 | 11/2008 | ............... H01J 49/14 |
| WO | WO 2013/073373 | 5/2013 | ............... H01J 49/10 |

(Continued)

OTHER PUBLICATIONS

The International Search Report and Written Opinion of the International Searching Authority for International Application No. PCT/US2019/020039 by Examiner D. Diez Schlereth dated May 16, 2019.

(Continued)

*Primary Examiner* — Michael Maskell
(74) *Attorney, Agent, or Firm* — Fish & Richardson P.C.

(57) ABSTRACT

The disclosure features methods and systems that include directing an ion beam to a region of a sample to liberate charged particles from the region of the sample, where the directed ion beam is pulsed at a first repetition rate, deflecting a first subset of the liberated charged particles from a first path to a second path different from the first path in response to a gate signal synchronized with the repetition rate of the pulsed ion beam, and detecting the first subset of the liberated charged particles in a time-of-flight (TOF) mass spectrometer to determine information about the sample, where the gate signal sets a common reference time for the TOF mass spectrometer for the first subset of charged particles liberated by each pulse of the ion beam.

30 Claims, 14 Drawing Sheets

(51) Int. Cl.
- *H01J 49/02* (2006.01)
- *G01N 33/68* (2006.01)
- *H01J 49/14* (2006.01)

(52) U.S. Cl.
CPC .......... *H01J 49/022* (2013.01); *H01J 49/025* (2013.01); *H01J 49/142* (2013.01)

(58) Field of Classification Search
USPC ................................. 250/281, 282, 286, 287
See application file for complete search history.

(56) References Cited

U.S. PATENT DOCUMENTS

| | | | |
|---|---|---|---|
| 8,853,623 B2 * | 10/2014 | Verenchikov | H01J 49/401 250/287 |
| 2015/0060656 A1 * | 3/2015 | Ugarov | H01J 49/061 250/282 |
| 2017/0178882 A1 * | 6/2017 | Bendall | H01J 49/40 |

FOREIGN PATENT DOCUMENTS

| | | | |
|---|---|---|---|
| WO | WO 2015/038784 | 3/2015 | ............. B01D 59/44 |
| WO | WO 2016/153819 | 9/2016 | ............. G01N 33/58 |

OTHER PUBLICATIONS

Borowsky, Award No. W81XWH-14-1-0192, "Next-Generation Molecular Histology Using Highly Multiplexed Ion-Beam Imaging (MIBI) of Breast Cancer Tissue Specimens for Enhanced Clinical Guidance", University of California, Davis, CA (Jan. 2018).

Leeat et al., "MIBI-TOF: A multi-modal multiplexed Imaging platform for Tissue pathology", URL:https://apps.dtic.mil/dtic/tr/fulltext/u2/1063950.pdf (Jan. 31, 2018).

* cited by examiner

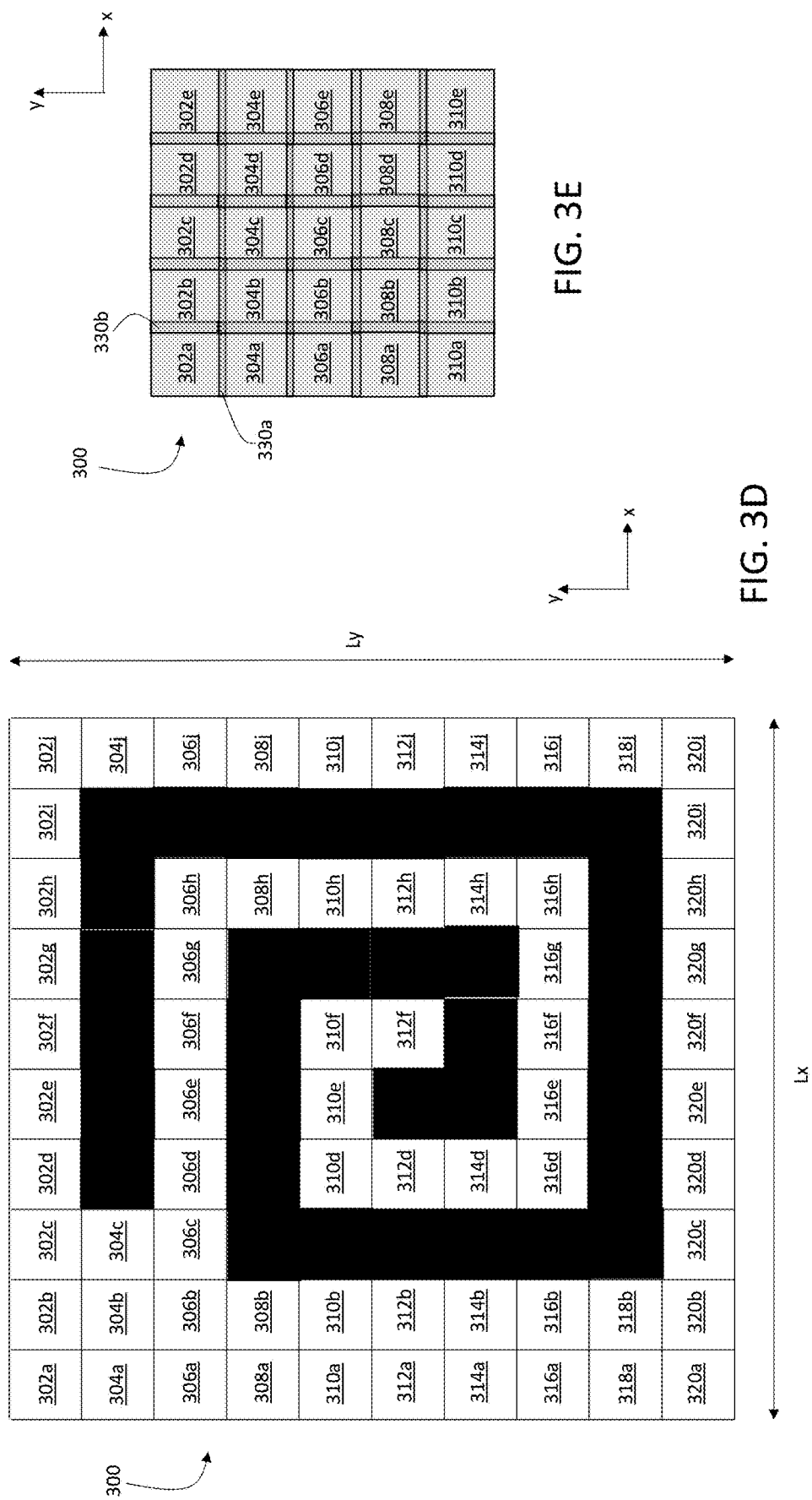

SOURCE-DETECTOR SYNCHRONIZATION IN MULTIPLEXED SECONDARY ION MASS SPECTROMETRY

CROSS-REFERENCE TO RELATED APPLICATIONS

This application claims priority to U.S. Provisional Application No. 62/636,220, filed on Feb. 28, 2018, the entire contents of which are incorporated herein by reference.

TECHNICAL FIELD

This disclosure relates to scanning of biological samples using an ion beam, and to determining mass spectrometry information for the samples based on ion beam exposure.

BACKGROUND

Immunohistochemistry methods have been used to visualize protein expression in biological samples such as tumor tissue biopsies. Such methods typically involve exposing a sample to antibodies coupled to fluorescent moieties or enzyme reporters that generate colored pigments. Analysis of spectral images of the tagged sample yields information that can be used to assess protein expression levels and co-expression events.

SUMMARY

This disclosure features multiplexed ion beam imaging methods for analyzing protein expression and other biological events and structures in tissue samples. Samples are tagged with antibodies conjugated to mass tags such as lanthanide elements and then exposed to a beam of primary ions. The primary ions are incident on the sample and generate secondary ions based on the mass tags. Spatial- and mass-resolved analysis of the secondary ions from the sample can provide information about protein expression and other biological events at specific sample locations.

Mass resolution of secondary ions can be achieved by measuring the time of flight of the ions. In one configuration for such measurements, secondary ions traveling from the sample are redirected into a new, typically orthogonal direction, thus resetting the time of flight of the ions in that direction. This type of orthogonal configuration allows the process of generating secondary ions by the ion beam source to be decoupled from the time of flight measurement of such ions. The ion beam can thus generate many more secondary ions in a short amount of time than with a linear instrument configuration that directly measures the time of flight of secondary ions generated by the ion beam. Measurement of a larger number of secondary ions can lead to increased sensitivity of the device. In addition, more data about the sample can be collected in a shorter amount of time.

The orthogonal configuration can be further improved by synchronizing the pulsing of the ion beam to the duty cycle of the measurement apparatus. With synchronization, a larger portion of secondary ions generated from the sample can be collected and measured.

Additional methods are disclosed for targeting specific ranges of mass tags for measurement using the orthogonal instrument configuration. Elimination of unwanted mass tags from measurement can lead to increased signal-to-noise ratio, further boosting the sensitivity of the measurements involving the tags of interest.

In general, in a first aspect, the disclosure features methods that include directing an ion beam to a region of a sample to liberate charged particles from the region of the sample, where the directed ion beam is pulsed at a first repetition rate, deflecting a first subset of the liberated charged particles from a first path to a second path different from the first path in response to a gate signal synchronized with the repetition rate of the pulsed ion beam, and detecting the first subset of the liberated charged particles in a time-of-flight (TOF) mass spectrometer to determine information about the sample, where the gate signal sets a common reference time for the TOF mass spectrometer for the first subset of charged particles liberated by each pulse of the ion beam.

Embodiments of the methods can include any one or more of the following features.

The TOF mass spectrometer can differentiate mass-to-charge ratio differences among the first subset of charged particles based on differences in detection time for their time-of-flight relative to the common reference time. The gate signal can be synchronized with the repetition rate of the pulsed ion beam to cause the first subset to comprise a substantial portion of at least one type of the liberated charged particles propagating along the first path. The substantial portion can include more than 50%, or preferably more than 70%.

The directed ion beam can have a pulse width of between 5 nanoseconds and 100 microseconds. (e.g., between 100 nanoseconds and 50 microseconds, between 1 microsecond and 50 microseconds). The first repetition rate can be between 1 kHz and 200 kHz (e.g., between 10 kHz and 100 kHz). The deflection from the first path to the second path can be between 60 degrees and 120 degrees. The gate signal can include a voltage pulse applied to an ion optic electrode to cause the deflection. The voltage pulse can have a pulse width of between 500 nanoseconds and 50 microseconds.

The liberated charged particles can travel along the first path at different speeds depending on their masses, and a delay between the voltage pulse and the pulsed ion beam can be set to select a certain range of charged particle masses to be in the first subset from among the liberated charged particles. The delay between the voltage pulse and the pulsed ion beam can be set to cause select heavier masses in the first subset of charged particles.

The methods can include blocking a second subset of the liberated charged particles propagating along the first path from entering a chamber containing the TOF mass spectrometer. The blocking can include using an adjustable mechanical stop and/or using adjustable electromagnetic fields generated by ion optic electrodes. The blocking of the second subset can occur during a time period different from the deflecting and can also be synchronized with the repetition rate of the pulsed ion beam.

The liberated charged particles can include secondary elemental atomic ions derived from mass tags associated with the sample. The pulsed ion beam can liberate the charged particles by ionizing the mass tags. The sample can be a planar sample that includes biological material on a conductive substrate.

The methods can include scanning the pulsed ion beam relative to the sample to irradiate additional regions of the sample, and further performing the deflecting and the detecting for each of the additional regions of the sample.

Embodiments of the methods can also include any of the other features disclosed herein, including features disclosed in connection with different embodiments, in any combination except as expressly stated otherwise.

In another aspect, the disclosure features mass spectroscopy systems that include: a pulsed ion source configured to direct an ion beam to a region of a sample to liberate charged particles from the region of the sample, where the pulsed ion source generates pulses of the ion beam at a first repetition rate; ion optics controllable to adjustably deflect a first subset of the liberated charged particles from a first path to a second path different from the first path; an ion optic controller coupled to the pulsed ion source and configured to generate a gate signal synchronized with the repetition rate of the pulsed ion beam to cause the ion optics to deflect the first subset from the first path to the second path; and a time-of-flight (TOF) mass spectrometer positioned to detect the first subset of the liberated charged particles to determine information about the sample, where the gate signal sets a common reference time for the TOF mass spectrometer for the first subset of charged particles liberated by each pulse of the ion beam.

Embodiments of the systems can include any one or more of the following features.

The TOF mass spectrometer can be configured to differentiate mass-to-charge ratio differences among the first subset of charged particles based on differences in detection time for their time-of-flight relative to the common reference time.

The gate signal can be synchronized with the repetition rate of the pulsed ion beam to cause the first subset to include a substantial portion of at least one type of the liberated charged particles propagating along the first path. The substantial portion can include more than 50%, or preferably more than 70%.

The directed ion beam can have a pulse width of between 5 nanoseconds and 100 microseconds (e.g., between 100 nanoseconds and 50 microseconds, between 1 microsecond and 50 microseconds). The first repetition rate can be between 1 kHz and 200 kHz (e.g., between 10 kHz and 100 kHz). The deflection from the first path to the second path can be between 60 degrees and 120 degrees.

The gate signal can include a voltage pulse, and the ion optic controller can be configured to apply the gate signal to an ion optic electrode to cause the deflection. The voltage pulse can have a pulse width of between 500 nanoseconds and 50 microseconds.

The liberated charged particles can travel along the first path at different speeds depending on their masses, and the ion optic controller can be configured to set a delay between the voltage pulse and the pulsed ion beam to select a certain range of charged particle masses to be in the first subset from among the liberated charged particles. For example, the ion optic controller can be configured to set the delay between the voltage pulse and the pulsed ion beam to cause select heavier masses in the first subset of charged particles.

The systems can include a blocking member positioned to block a second subset of the liberated charged particles propagating along the first path from entering a chamber containing the TOF mass spectrometer. The blocking member can include an adjustable mechanical stop. The ion optic controller can be configured to generate one or more electromagnetic fields using ion optic electrodes to direct the second subset of the liberated charged particles to be incident on the blocking member. The blocking of the second subset can occur during a time period different from the deflecting and can also be synchronized with the repetition rate of the pulsed ion beam.

The liberated charged particles can include secondary elemental atomic ions derived from mass tags associated with the sample. The pulsed ion beam can liberate the charged particles by ionizing the mass tags. The sample can be a planar sample that includes biological material on a conductive substrate.

The ion optic controller can be configured to generate one or more control signals that cause the pulsed ion source to scan the pulsed ion beam relative to the sample to irradiate additional regions of the sample, and generate one or more control signals that cause the ion optics to adjustably deflect a first subset of liberated charged particles corresponding to each additional region from a first path to a second path different from the first path. The TOF mass spectrometer can be configured to detect the first subset of the liberated charged particles corresponding to each additional region.

Embodiments of the systems can also include any of the other features disclosed herein, including features disclosed in connection with different embodiments, in any combination except as expressly stated otherwise.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 3A-E are a schematic diagrams showing various exposure patterns of a primary ion beam on a sample.

Like reference numbers and designations in the various drawings indicate like elements.

DETAILED DESCRIPTION

A. General Overview—Multiplexed Ion Beam Imaging Systems

Multiplexed visualization of protein expression and other biochemical moieties and structures allows researchers to identify important correlations between biological functional events. Visualization of protein expression can be used to assess malignancies in excised tissue samples as part of a diagnostic work-up, and in particular, to provide important information about signaling pathways and correlated structural development in tumor tissue.

This disclosure features systems and methods for performing multiplexed visualization of antigens and other biochemical structures and moieties in biological samples using secondary ion mass spectrometry. Structure-specific antibodies are conjugated to specific mass tags, typically in the form of metallic elements (e.g., lanthanide elements). When a sample is exposed to the conjugated antibody-mass tag labels, the labels bind to corresponding antigens. Exposure of the labeled sample to a primary ion beam liberates secondary ions corresponding to the conjugated mass tags from the labeled sample. Performing spatially-resolved detection of the secondary ions that are generated from the sample allows direct visualization of the localization of specific antigens in the sample, and extraction of quantitative information (e.g., antigen concentration) as a function of spatial location. This information can be combined with other structural information (e.g., information about tumor margins, cell types/morphologies) to develop a detailed assessment of tumor viability and progression in the sample.

Figure 1:
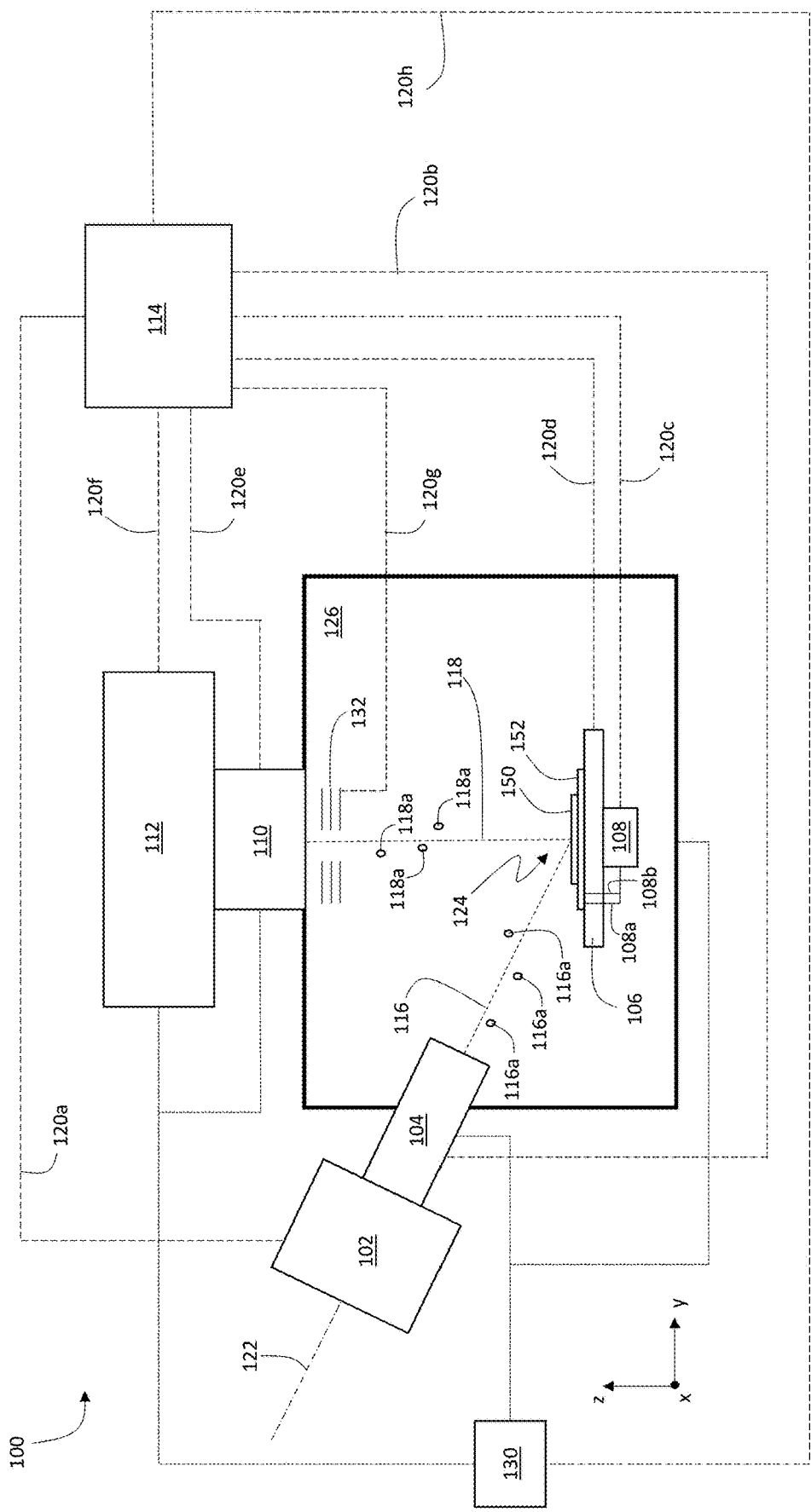
FIG. 1 is a schematic diagram showing an example system for multiplexed ion beam imaging.

FIG. 1 is a schematic diagram showing an example system 100 for multiplexed ion beam imaging. System 100 includes an ion beam source 102, ion beam optics 104, a stage 106, a voltage source 108, ion collecting optics 110, and a detection apparatus 112. Each of these components is connected to a controller 114 via signal lines 120a-120h. During operation of system 100, controller 114 can adjust operating parameters of each of ion beam source 102, ion beam optics 104, stage 106, voltage source 108, ion collecting optics 110, pressure regulation system 130, and detection apparatus 112. Further, controller 114 can exchange information with each of the foregoing components of system 100 via signal lines 120a-120h.

During operation, ion beam source 102 generates an ion beam 116 that includes a plurality of primary ions 116a. Ion beam 116 is incident on a sample 150 that is positioned on stage 106 inside sample chamber 126. Optionally, in certain embodiments, voltage source 108 applies an electrical potential to a substrate 152 that supports sample 150. Primary ions 116a in ion beam 116 interact with sample 150, generating secondary ions 118a as a secondary ion beam 118. Secondary ions 118a are attracted to and focused by extractor electrodes 132 into the ion optics 110. Secondary ion beam 118 is collected by ion collecting optics 110 and directed into detection apparatus 112. Detection apparatus 112 measures one or more ion counts corresponding to secondary ions 118a in secondary ion beam 118 and generates electrical signals corresponding the measured ion counts. Controller 114 receives the measured electrical signals from detection apparatus 112 and analyzes the electrical signals to determine information about secondary ions 118a and sample 150.

Controller 114 can adjust a wide variety of different operating parameters of the various components of system 100, and can transmit information (e.g., control signals) and receive information (e.g., electrical signals corresponding to measurements and/or status information) from the components of system 100. For example, in some embodiments, controller 114 can activate ion beam source 102 and can adjust operating parameters of ion beam source 102, such as an ion current of ion beam 116, a beam waist of ion beam 116, and a propagation direction of ion beam 116 relative to central axis 122 of ion beam source 102. In general, controller 114 adjusts the operating parameters of ion beam source 102 by transmitting suitable control signals to ion beam source 102 via signal line 120a. In addition, controller 114 can receive information from ion beam source 102 (including information about the ion current of ion beam 116, the beam waist of ion beam 116, the propagation direction of ion beam 116, and various electrical potentials applied to the components of ion beam source 102) via signal line 120a.

A variety of different primary ion beams 116 generated by ion source 102 can be used to expose sample 150. In some embodiments, for example, primary ion beam 116 consists of a plurality of oxygen ions. In certain embodiments, primary ion beam 116 includes a plurality of one or more of gallium ions, helium ions, cesium ions, neon ions, krypton ions, xenon, and/or argon ions.

For example, in some embodiments, ion source 102 can be implemented as an oxygen duoplasmatron source (e.g., Direct Extraction Negative Ion Duoplasmatron, available from National Electrostatics Corp., Middleton, Wis.), which generates primary ion beam 116. Alternatively, or additionally, ion source 102 can be implemented as a Cs liquid metal ion gun, as described for example in Umemura et al., *Rev. Sci. Instrum.* 65, 2276 (1994), available at https://doi.org/10.1063/1.1144676), the entire contents of which are incorporated herein by reference.

Ion beam optics 104 generally include a variety of elements that use electric fields and/or magnetic fields to control attributes of ion beam 116. In some embodiments, for example, ion beam optics 104 include one or more beam focusing elements that adjust a spot size of ion beam 116 at a location of incidence 124 of ion beam 116 on sample 150. In certain embodiments, ion beam optics 104 include one or more beam deflecting elements that deflect ion beam 116 relative to axis 122, thereby adjusting the location of incidence 124 of ion beam 116 on sample. Ion beam optics 104 can also include a variety of other elements, including one or more apertures, extraction electrodes, beam blocking elements, and other elements that assist in directing ion beam 116 to be incident on sample 150.

Controller 114 can generally adjust the properties of any of the foregoing elements via suitable control signals transmitted via signal line 120b. For example, controller 114 can adjust the focusing properties of one or more beam focusing elements of ion beam optics 104 by adjusting electrical potentials applied to the beam focusing elements via signal line 120b. Similarly, controller 114 can adjust the propagation direction of ion beam 116 (and the location of incidence 124 of ion beam 116 on sample 150) by adjusting electrical potentials applied to the beam deflection elements via signal line 120b. Further, controller 114 can adjust positions of one or more apertures and/or beam blocking elements in ion beam optics 104, and adjust electrical potentials applied to extraction electrodes in ion beam optics 104, via suitable control signals transmitted on signal line 120b. In addition to adjusting properties of ion beam optics 104, controller 114 can receive information from various components of ion beam optics 104, including information about electrical potentials applied to the components of ion beam optics 104 and/or information about positions of the components of ion beam optics 104.

Stage 106 includes a surface for supporting sample 150 (and substrate 152). In general, stage 106 can be translated in each of the x-, y-, and z-coordinate directions. Controller 114 can translate stage 106 in one of the above directions by transmitting control signals on signal line 120d. To effect a translation of the location of incidence 124 of ion beam 116 on sample 150, controller 114 can adjust one or more electrical potentials applied to deflection elements of ion beam optics 104 (e.g., to deflect ion beam 116 relative to axis 122), adjust the position of stage 106 via control signals transmitted on signal line 120d, and/or adjust both deflection elements of ion beam optics 104 and the position of stage 106. In addition, controller 114 receives information about the position of stage 106 transmitted along signal line 120d.

In some embodiments, system 100 includes a voltage source 108 connected to substrate 152 via electrodes 108a and 108b. When activated by controller 114 (via suitable control signals transmitted on signal line 120c), voltage source 108 applies an electrical potential to substrate 152. The applied electrical potential assists in the capture of secondary ion beam 118 from sample 150, as the electrical potential repels secondary ions 118a, causing the secondary ions to leave sample 150 in the direction of ion collecting optics 110.

As shown in FIG. 1, sample 150 is typically a relatively planar sample that extends in the x- and/or y-coordinate directions and has a thickness measured in the z-coordinate direction. The support surface of stage 106 likewise extends in the x- and y-coordinate directions.

In some embodiments, system 100 includes extractor electrodes 132. Controller 114 can activate extractor electrodes 132 by applying suitable electrical potentials (e.g., via signal line 120g) to the extractor electrodes. The applied electrical potential, which represents a potential difference relative to the electrical potential applied to substrate 152, generates an electric field that accelerates secondary ions 118a away from the sample and towards extractor electrodes 132.

Controller 114, via signal line 120e, applies an electrical potential to one or more elements of the ion collecting optics 110 to create a potential difference between extractor electrodes 132 and the elements of ion collection optics 110. The potential difference accelerates secondary ions 118a collected by extractor electrodes 132 up to a predetermined energy, efficiently transferring secondary ions 118a from extractor electrodes 132 to ion collection optics 110. As a result, secondary ion beam 118 consisting of a plurality of secondary ions 118a is captured by ion collecting optics 110.

In general, ion collecting optics 110 can include a variety of electric and magnetic field-generating elements for deflecting and focusing secondary ion beam 118. In addition, ion collecting optics 100 can include one or more apertures, beam blocking elements, and electrodes. As discussed above in connection with ion beam optics 104, controller 114 can adjust electrical potentials applied to each of the components of ion collecting optics 110 via suitable control signals transmitted on signal line 120e. Controller 114 can also adjust the positions of apertures, beam blocking elements, and other movable components of ion collecting optics 110 by transmitting control signals on signal line 120e. In addition, controller 114 can receive information about operating parameters (e.g., voltages, positions) of various components of ion collecting optics 110 on signal line 120e.

Ion collecting optics 110 direct secondary ion beam 118 into detection apparatus 112. Detection apparatus 112 measures ion counts or currents corresponding to the various types of secondary ions 118a in secondary ion beam 118, and generates output signals that contain information about the measured ion counts or currents. Controller 114 can adjust various operating parameters of detection apparatus 112, including maximum and minimum ion count detection thresholds, signal integration times, the range of mass-to-charge (m/z) values over which ion counts are measured, the dynamic range over which ion counts are measured, and electrical potentials applied to various components of detection apparatus 112, by transmitting suitable control signals over signal line 120f.

Controller 114 receives the output signals from detection apparatus that include information about the measured ion counts or currents on signal line 120f. In addition, controller 114 also receives operating parameter information for the various components of detection apparatus 112 via signal line 120f, including values of the various operating parameters discussed above.

Detection apparatus 112 can include a variety of components for measuring ion counts/currents corresponding to secondary ion beam 118. In some embodiments, for example, detection apparatus 112 can correspond to a time-of-flight (TOF) detector. In certain embodiments, detection apparatus 112 can include one or more ion detectors such as Faraday cups, which generate electrical signals when ions are incident on their active surfaces. In some embodiments, detection apparatus 112 can be implemented as a multiplying detector, in which incident ions enter an electron multiplier where they generate a corresponding electron burst. The electron burst can be detected directly as an electrical signal, or can be incident on a converter that generates photons (i.e., an optical signal) in response to the incident electrons. The photons are detected with an optical detector which generates the output electrical signal.

In some embodiments, sample chamber 126, ion optics 110, and detection apparatus 112 are maintained under reduced pressure using pressure regulation system 130. For example, pressure regulation system 130 can maintain a pressure of $1.0 \times 10^{-4}$ Torr or less (e.g., $1.0 \times 10^{-5}$ Torr or less, $1.0 \times 10^{-6}$ Torr or less, $1.0 \times 10^{-7}$ Torr or less, $1.0 \times 10^{-8}$ Torr or less, $1.0 \times 10^{-10}$ Torr or less) within one or more components of the system, including ion source 102, ion beam optics 104, sample chamber 126, ion optics 110, and detection apparatus 112.

Pressure regulation system 130 can maintain equal pressures in two or more different components, or even all components, of the system. Alternatively, pressures in certain components can differ. In some embodiments, for example, pressure regulation system 130 can individually regulate gas pressures in each of ion source 102, ion beam optics 104, sample chamber 126, ion optics 110, and detection apparatus 112, such that the gas pressure in each component can independently fall within any of the above ranges. Gas pressures in any these components can be different or the same, depending upon the nature of the sample, the signals being measured, and different operating conditions within the system.

Pressure regulation system 130, communicates the pressure of these components over line 120h to controller 114. Based on this information, controller 114 can adjust operating parameters of system 130 over line 120h to achieve and maintain lowered pressure in these separate components.

Operation at reduced pressure can help to reduce contamination and/or signal noise in system 100. For instance, lowered pressure can reduce the number of undesirable particles in the system that are detected. Detection of such particles can lead to increased background noise and potential saturation of the detector.

Reduced pressure operation can also reduce the number of undesirable particles in the system that can react with or collide into generated secondary ions traveling from sample 150 to detection apparatus 112. In addition to modifying the energy distribution of ions of interest, collisions between the secondary ions and such undesirable particles can cause the secondary ions to fragment prematurely via undesirable fragmentation pathways, leading to a reduction of the secondary ion molecular ion peak signal intensity.

In addition, in certain embodiments, maintaining a reduced pressure in the system during operation can assist with ion transport within the system. For example, by maintaining different portions of the system at different reduced pressures during operation, pressure gradients between the different portions of the system can be established, and transport of the secondary ions between the different portions of the system can be aided by the pressure gradients.

As discussed above, controller 114 is capable of adjusting a wide variety of operating parameters of system 100, receiving and monitoring values of the operating parameters, and receiving electrical signals containing information about secondary ions 118*a* (and other species) generated from sample 150. Controller 114 analyzes the electrical signals to extract the information about secondary ions 118*a* and other species. Based on the extracted information, controller 114 can adjust operating parameters of system 100 to improve system performance (e.g., m/z resolution, detection sensitivity) and to improve the accuracy and reproducibility of data (e.g., ion counts) measured by system 100. Controller 114 can also execute display operations to provide system users with images of sample 150 that show distributions of various mass tags within sample 150, and storage operations to store information relating to the distributions in non-volatile storage media.

Figure 2:
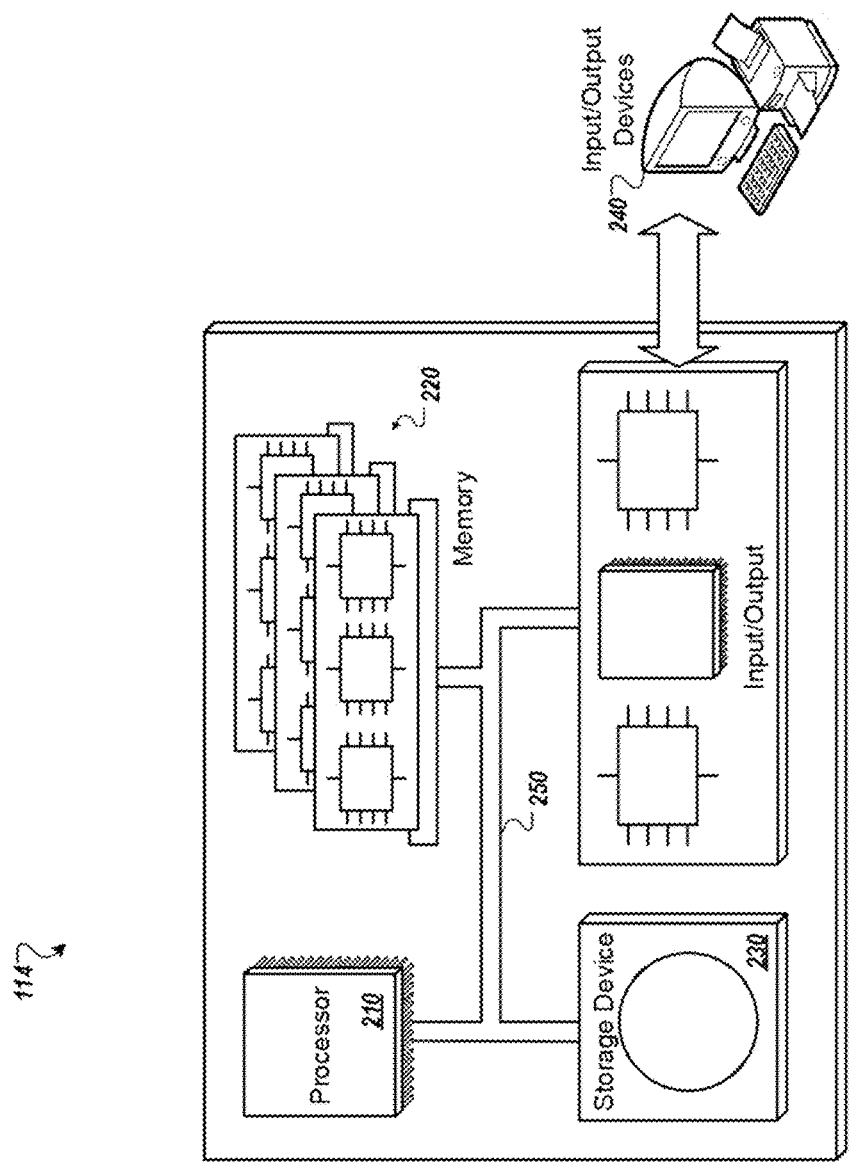
FIG. 2 is a schematic diagram of a controller and auxiliary devices.

As discussed above, any of the steps and functions described herein can be executed by controller 114. In general, controller 114 can include a single electronic processor, multiple electronic processors, one or more integrated circuits (e.g., application specific integrated circuits), and any combination of the foregoing elements. Software- and/or hardware-based instructions are executed by controller 114 to perform the steps and functions discussed herein. As shown in FIG. 2, controller 114 can include a processor 210 and a data storage system (including memory 220 and/or storage elements e.g., storage device 230), interconnected using a system bus 250. The controller can be connected to at least one input device, and at least one output device, such as a display 240. Each set of software-based instructions, embodied as a software program stored on a tangible, non-transient storage medium (e.g., an optical storage medium such as a CD-ROM or DVD, a magnetic storage medium such as a hard disk, or a persistent solid state storage medium) or device, can be implemented in a high-level procedural or object-oriented programming language, or an assembly or machine language.

B. Sample Exposure and Secondary Ion Image Formation

Multiplexed Ion Beam Imaging (MIBI) is a surface sensitive technique that allows for detection and localization of various chemical compositions on biological sample surfaces. For example, MIBI methods may be used to resolve single molecular targets (e.g., individual RNA molecules, DNA molecules, proteins, or protein complexes) or to assay a biological sample of cells (e.g., for the amount of certain proteins, nucleic acids or molecules). "Multiplexing" in MIBI refers to the use of multiple labels to simultaneously or sequentially detect and measure multiple analytes in a single biological sample.

MIBI methods offer numerous advantages over conventional multiplexed immunohistochemical techniques for visualizing protein expression. For example, conventional techniques rely on optical detection of fluorescence emission from a sample that has been labeled with multiple antibody-conjugated flurophores. The conjugated fluorophores bind specifically to corresponding antigens in the sample, and imaging of fluorescence emission from the sample is used to assess the spatial distribution of the fluorophores. For samples in which antigen concentrations are relatively low, signal amplification (e.g., using multivalent, enzyme-linked secondary antibodies) can be used to aid visualization. However, the use of signal amplification techniques can compromise quantitative information (e.g., antigen concentration information) that might otherwise be extracted from sample images.

In conventional multiplexed immunohistochemical visualization techniques, other constraints can also be encountered. Optical detection and separation of spectral signatures of multiple fluorophores is a complex problem, particularly where the fluorescence spectra of the fluorophores exhibit significant overlap. Without robust discrimination between spectral signatures of the fluorophores, important expression-related information may not be uncovered. Further, such techniques often rely on primary antibodies generated in dissimilar host species. These factors can limit the utility of conventional multiplexed immunohistochemical visualization techniques for predictive biomarker development and clinical diagnostics.

In contrast, MIBI methods can be used to simultaneously resolve spatial distributions of relatively large numbers of mass tags applied to samples, with image resolution comparable to optical microscopy at high magnification. In addition, images acquired by MIBI techniques do not suffer signal overlap problems and allow for highly precise quantification of antigen concentration. They are not subject to antibody incompatibility arising from host-target mismatches.

Methods for labeling sample 150 with suitable mass tags (e.g., antibody-conjugated mass tags) will be discussed in a subsequent section. After sample 150 has been labeled, to perform multiplexed ion beam imaging, primary ion beam 116 is directed to multiple different locations of incidence 124 on sample 150. At each location 124, primary ion beam 116 generates secondary ions 118*a* by ionizing molecular species from the sample surface. Specifically, the secondary ions 118*a* correspond to portions of the mass tags that are antibody-conjugated and bound to sample 150 at that location.

The secondary ions 118*a*—which form secondary ion beam 118—are measured and analyzed to determine spatially resolved information about the biochemical structure of sample 150. For example, secondary ions 118*a* are transferred into detection apparatus 112, such as a mass spectrometer, where they are mass analyzed and quantified using standard mass analysis techniques (e.g., time-of-flight, magnetic sector, quadrupole, ion trap, and combinations thereof). Using a time of flight ("TOF") technique, secondary ions 118*a* can be separated by their flight time through detection apparatus 112, the flight time corresponding to the mass of that ion. In other words, a measurement of the time between generation and detection of the secondary ions (flight time) enables the analysis of masses of the generated secondary ions to be performed. Suitable methods for detection and quantification of second ions 118*a* will be discussed more extensively in a later section.

To obtain spatially resolved information from sample 150, primary ion beam 116 is translated across sample 150 to multiple different locations of incidence 124. The multiple different locations of incidence form a two-dimensional exposure pattern of primary ion beam 116 in the plane of sample 150 (i.e., in a plane parallel to the x-y plane). The mass spectra that are collected from the sample at each location along the sample surface can be used to generate a two-dimensional (2D), spatially resolved image of the scanned portion of the sample. At each location, mass spectral information about secondary ions 118a detected from that location is determined. Accordingly, at each pixel in the resulting image, mass spectral information corresponding to different mass tags bound to the sample at the location corresponding to the pixel is obtained.

Figure 3A:
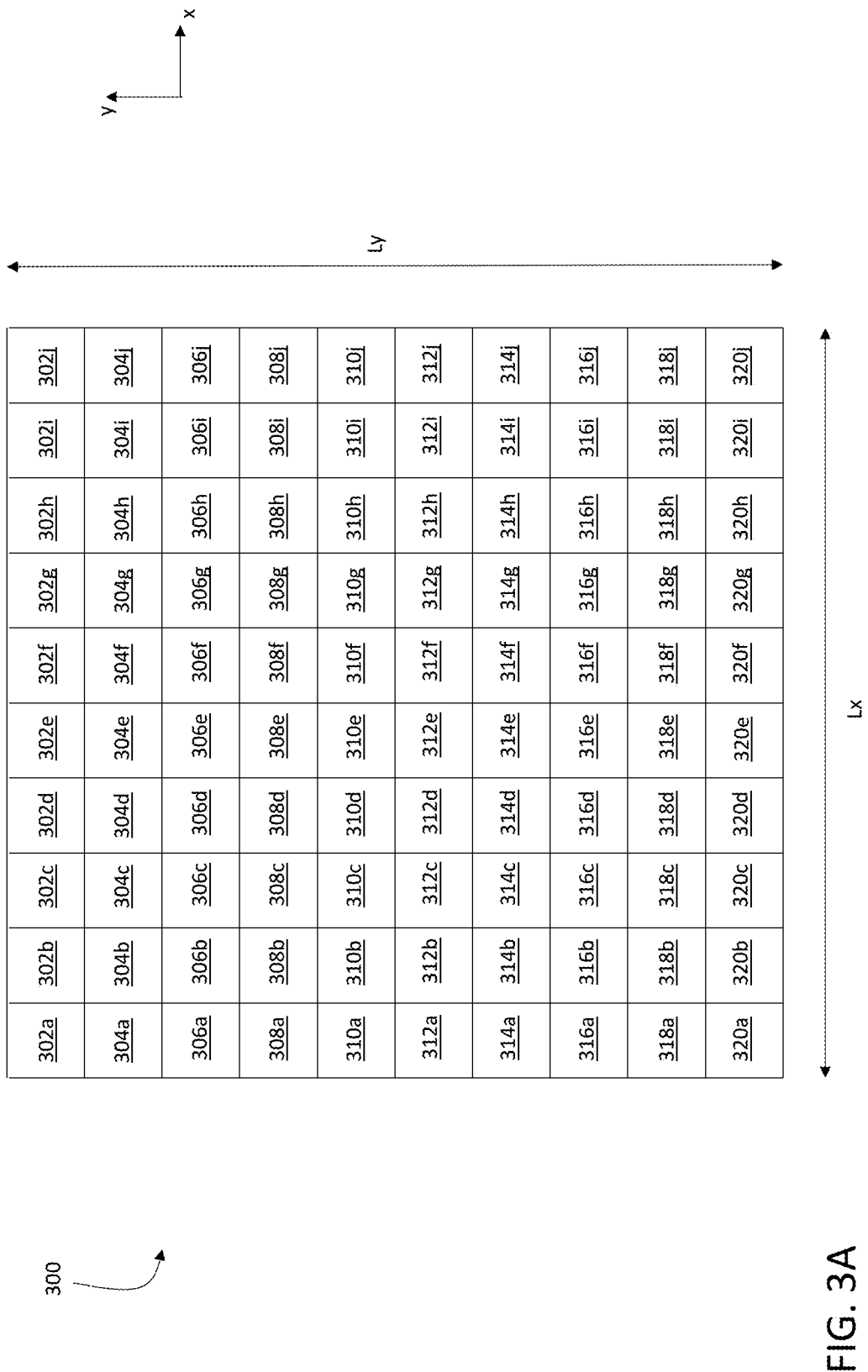

In general, a wide variety of different exposure patterns can be used. In some embodiments, for example, the exposure pattern corresponds to a square or rectangular array of locations of incidence 124 of primary ion beam 116 on sample 150. FIG. 3A is a schematic diagram showing a square array of locations of incidence 124 of primary ion beam 116 on sample 150, forming a square exposure pattern 300 on sample 150. Each row of exposure pattern 300 includes 10 distinct locations of incidence 124 of primary ion beam 116 on sample 150, spaced along the x-coordinate direction. Each column of exposure pattern 300 includes 10 distinct locations of incidence 124 of primary ion beam 116 on sample 150, spaced along the y-coordinate direction. In total, exposure pattern 300 includes 100 distinct locations of incidence 124 of primary ion beam 116.

In general, each row and column of exposure pattern 300 can include any number of distinct locations of incidence 124 of primary ion beam 116 on sample 150. For example, in some embodiments, each row and/or column of exposure pattern 300 includes 10 or more (e.g., 20 or more, 30 or more, 50 or more, 100 or more, 200 or more, 300 or more, 500 or more, 1000 or more) distinct locations of incidence 124 of primary ion beam 116.

To expose sample 150 to primary ion beam 116 according to an exposure pattern, the different locations of incidence 124 constituting exposure pattern 300 can generally be visited in any order by primary ion beam 116. In some embodiments, however, the different locations of incidence 124 are visited in certain sequences. For example, the square exposure pattern 300 in FIG. 3A can be implemented such that primary ion beam 116 is scanned along each row of the exposure pattern in sequence. After visiting each location of incidence 124 in a single row in sequence (e.g., by translating primary ion beam 116 parallel to the x-coordinate direction), primary ion beam 116 is translated parallel to the y-coordinate direction to the next row in exposure pattern 300, and then visits each location of incidence 124 in the next row in sequence.

This example sequence of exposures corresponds to a pattern of raster-scanning of primary ion beam 116 on sample 150. As shown in FIG. 3A, locations 302a-302j are each visited in sequential order by primary ion beam 116, followed by locations 304a-304j in sequential order, and so on in sequence until the final row of locations 320a-320j is visited in sequential order.

Exposure pattern 300 includes a total of 100 distinct locations of incidence of primary ion beam 116 on sample 150. More generally, however, exposure pattern 300 can include any number of distinct locations of incidence of primary ion beam 116. In certain embodiments, for example, exposure pattern 300 includes 25 or more (e.g., 50 or more, 100 or more, 200 or more, 500 or more, 1000 or more, 5000 or more, 10000 or more, 20000 or more, 30000 or more, 50000 or more, 100000 or more, 200000 or more, 500000 or more) distinct locations of incidence of primary ion beam 116 on sample 150.

A maximum dimension of exposure pattern 300 measured in a direction parallel to the x-coordinate direction is Lx, and a maximum dimension of exposure pattern 300 measured in a direction parallel to the y-coordinate direction is Ly. In general, Lx and Ly are selected as desired according to the spatial dimensions of the portion of sample 150 to be analyzed. For example, in some embodiments, Lx and Ly can each independently be 25 microns or more (e.g., 50 microns or more, 100 microns or more, 200 microns or more, 300 microns or more, 400 microns or more, 500 microns or more, 700 microns or more, 1.0 mm or more, 1.5 mm or more, 2.0 mm or more, 2.5 mm or more, 3.0 mm or more, 5.0 mm or more).

Figure 3C:
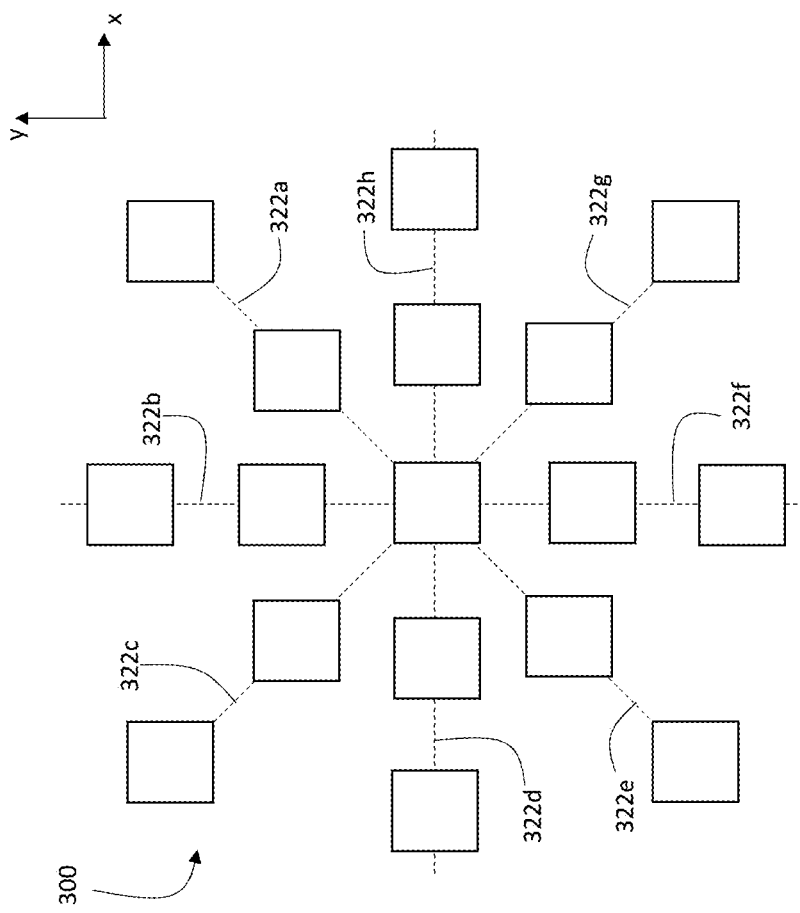
Figure 3B:
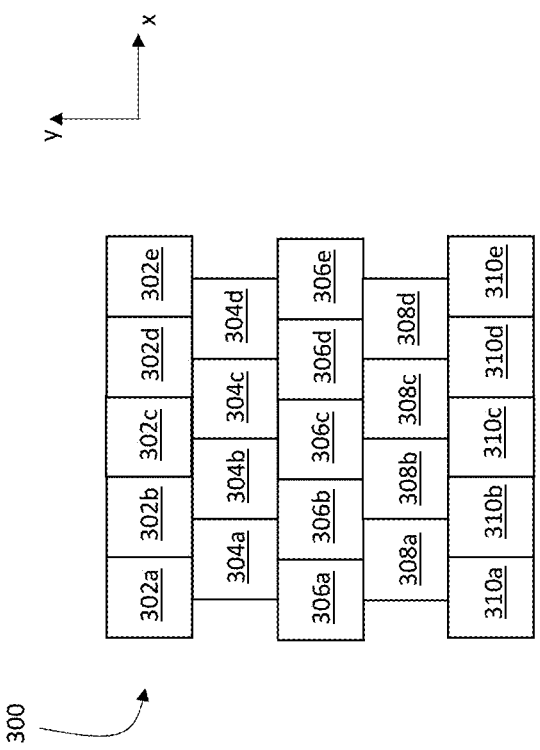

Exposure pattern 300 in FIG. 3A is a square pattern. More generally, however, the exposure pattern formed by the set of locations of incidence 124 of primary ion beam 116 on sample 150 need not be square or rectangular. Two-dimensional exposure patterns having a variety of different shapes and spacings between locations of incidence of primary ion beam 116 can be implemented. For example, the array may be hexagonal, or have an irregular (e.g., random or spatially varying) shape. FIG. 3B is a schematic diagram showing an exposure pattern 300 in which rows of the exposure pattern are offset spatially in the y-direction, forming an offset array. FIG. 3C is a schematic diagram showing a radial exposure pattern 300 in which individual locations of incidence of primary ion beam 116 are exposed in sequence along radial lines 322a-322h.

FIG. 3D is a schematic diagram showing a spiral exposure pattern 300 on the square array shown in FIG. 3A. The dark squares indicate individual locations of incidence of primary ion beam 116 exposed in sequence along the spiral, starting with location 312e and ending with location 304d.

FIG. 3E is a schematic diagram showing a square exposure pattern 300 where the locations of incidence 302a-310e overlap, e.g., at darker shaded regions 330a and 330b. The extent of overlap between the locations of incidence can generally be selected as desired for particular samples and measurement applications.

Returning to FIG. 3A, when sample 150 is exposed to primary ion beam 116 according to exposure pattern 300, the exposure can be implemented based on a single execution of exposure pattern 300 or based on multiple executions of exposure pattern 300. In other words, in some embodiments, sample 150 is exposed to primary ion beam 116 by directing primary ion beam 116 to visit each location in exposure pattern 300 once. In certain embodiments, sample 150 is exposed to primary ion beam 116 by directing primary ion beam 116 to visit each location in exposure pattern 300 multiple times. Typically, for example, after primary ion beam 116 has visited each location in exposure pattern 300 once, primary ion beam 116 follows a second exposure sequence in which the beam visits the locations in exposure pattern 300 a second time. Subsequent exposure sequences can be implemented in which primary ion beam 116 repeats the sequence of exposures defined by exposure pattern 300 as many times as desired.

In certain embodiments, exposure to primary ion beam 116 at each location in exposure pattern 300 can occur multiple times before the primary ion beam is moved to a new location in exposure pattern 300. That is, at each location in the pattern, the sample can be exposed to primary ion beam 116 two or more times (e.g., three or more times, four or more times, five or more times, seven or more times) before primary ion beam 116 moves to the next location in the pattern. Exposing the sample to primary ion beam 116 in such a manner can have certain advantages. For example, where multiple exposures of the sample to the primary ion beam 116 are desired, exposing the sample in this manner can reduce the overall amount of time required for sample scanning by reducing the number of times that primary ion beam 116 is translated.

In general, the accuracy and reproducibility of the ion counts/currents measured by detection apparatus 112 depends on number of secondary ions 118a generated by the interaction between primary ion beam 116 and sample 150. The number of secondary ions generated at each location of incidence 124 of primary ion beam 116 is in turn a function of the total primary ion dose at each location. As the primary ion dose increases, all other factors being held constant, the number of secondary ions generated also increases. As discussed above, the total dose of primary ions at each location of incidence 124 can be delivered via a single exposure to primary ion beam 116 at each location, or via multiple exposures to primary ion beam 116 at each location (i.e., by repeating exposure pattern 300).

In summary, as used herein, the term "exposure pattern"—examples of which are represented schematically by exposure patterns 300 in FIGS. 3A-3E—refers to the set of spatial locations of incidence of primary ion beam 116 on sample 150, as well as the set of dwell times (also referred to as exposure times), ion doses, ion beam currents, and other exposure parameters associated with each of the spatial locations of incidence of primary ion beam 116 on sample 150. In some embodiments, controller 114 maintains information corresponding to the exposure pattern in a volatile and/or non-volatile memory unit. During operation of system 100, controller 114 can modify the exposure pattern—by modifying the set of locations of incidence of primary ion beam 116 associated with the exposure pattern, and/or by modifying any of the exposure parameters associated with the set of spatial locations—in response to ion counts/currents measured by detection apparatus 112, and/or to adjust performance-related metrics for system 100 such as signal resolution, signal-to-noise ratio, and data reproducibility and/or accuracy.

The above discussion of "exposure patterns" can also take into account the cross-sectional shape of the ion beam at location of incidence 124, which corresponds to a spatial cross-sectional distribution of ions within the ion beam at location of incidence 124. In general, depending upon the nature of ion source 102 and ion beam optics 104, a number of different cross-sectional shapes of the ion beam can be used. In some embodiments, for example, the cross-sectional shape can be circular or elliptical, such that the ion distribution within the cross-sectional area of the beam is approximately uniform. The cross-sectional shape of ion beam 116 on the sample surface can depend on the direction of propagation of the ion beam relative to the sample surface. For example, in certain embodiments, the cross-sectional shape of ion beam 116 on the sample surface can be elliptical when ion beam 116 is incident on the surface at a non-orthogonal angle.

In some embodiments, the cross-sectional shape of ion beam 116 on the sample surface can reflect a spatially varying distribution of ions within the ion beam. For example, the cross-sectional shape of ion beam 116 can be Gaussian or, more generally, reflect another spatial ion distribution within the ion beam in which ion density is largest at the center of the beam, and decreases toward the edges of the beam. More complex shapes are also possible in which the ion density reaches local maximum values at multiple locations within the cross-sectional area of ion beam 116, effectively forming a "multipole" cross-sectional shape. Dipolar, quadrupolar, hexapolar, and octapolar cross-sectional shapes can be formed via suitable configuration of ion source 102 and ion beam optics 104.

In some embodiments, to control the location of incidence 124 of primary ion beam 116 on sample 150, controller 114 translates stage 106 in the x- and y-coordinate directions via control signals transmitted on signal line 120d. With primary ion beam 116 directed to a static location, motion of stage 106 in the x- and y-coordinate directions effects translations of sample 150 in the x- and y-coordinate directions relative to the location of primary ion beam 116, thereby moving the location of incidence 124 of primary ion beam 116.

Figure 4:
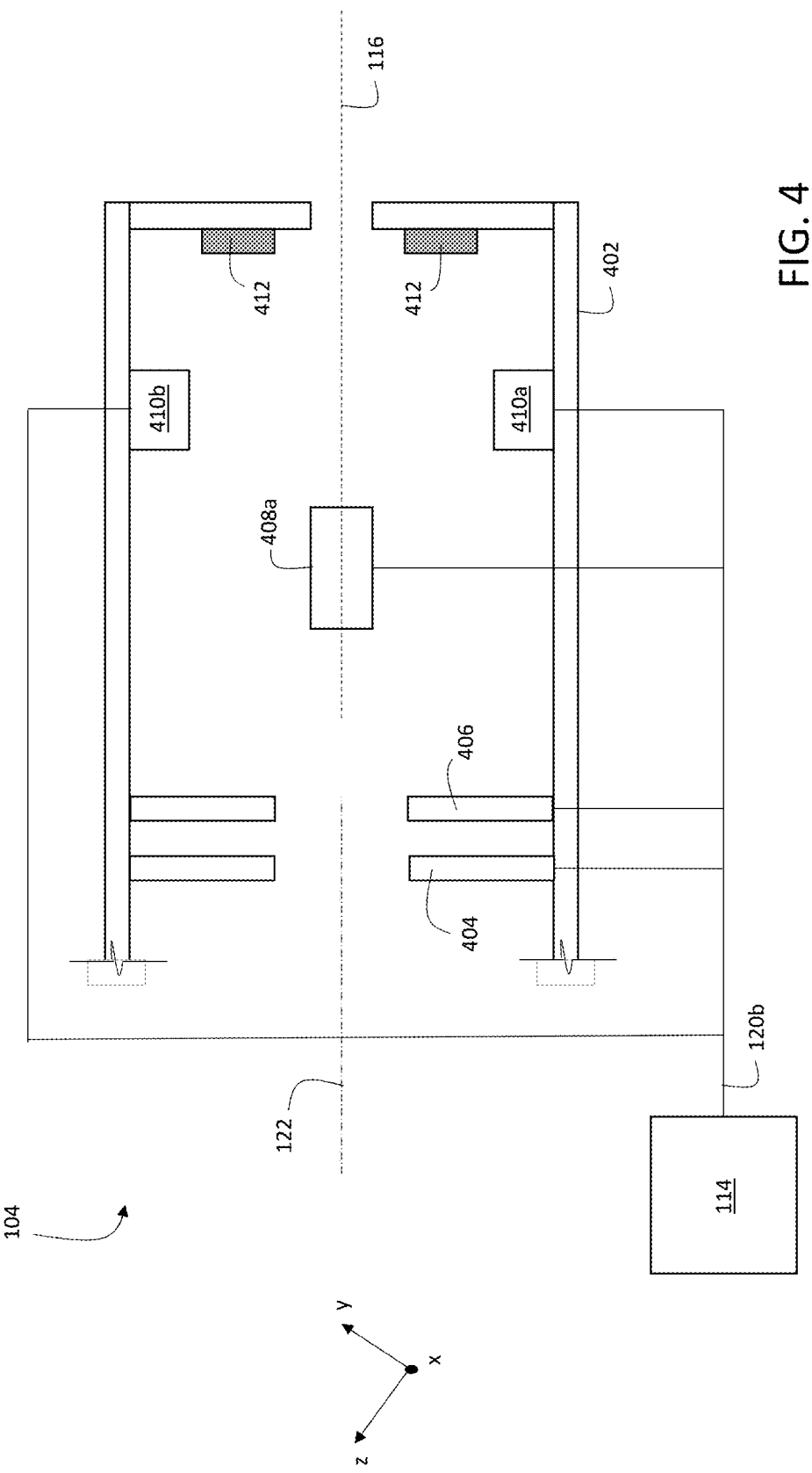
FIG. 4 is a schematic diagram showing an example of a portion of ion beam optics.

Alternatively, or in addition, in certain embodiments controller 114 adjusts one or more elements of ion beam optics 104 to translate the location of primary ion beam 116 on sample 150. FIG. 4 is a schematic diagram showing an example of a portion of ion beam optics 104. Ion beam optics 104 include a housing 402 that encloses a variety of components, including focusing elements 404 and 406 (implemented as annular electrostatic lenses), a first pair of deflection electrodes (only one of which, electrode 408a, is shown in FIG. 4 due to the perspective of the figure), and a second pair of deflection electrodes 410a and 410b. Ion beam optics 104 also include beam blocking elements 412.

Controller 114 is electrically connected to focusing elements 404 and 406, to the first pair of deflection electrodes (shown via a connection to electrode 408a in FIG. 4), and to the second pair of deflection electrodes 410a and 410b, via signal line 120b. Controller 114 adjusts electrical potentials applied to each of the elements to which it is connected by transmitting appropriate signals on signal line 120b.

During operation of system 100, primary ion beam 116 enters ion beam optics 104 through an aperture (not shown in FIG. 4) in housing 502, propagating nominally along central axis 122 of ion beam optics 104. By applying suitable electrical potentials to annular focusing elements 404 and 406, controller 114 adjusts the focal position of primary ion beam 116 along axis 122.

Controller 114 can adjust the location of incidence 124 of primary ion beam 116 on sample 150 by adjusting electrical potentials applied to the first and second pairs of deflection electrodes via control signals transmitted along signal line 120b. For example, by adjusting the electrical potentials applied to the first pair of deflection electrodes (electrode 408a and a cooperating second electrode not shown in FIG. 4), primary ion beam 116 is deflected in a direction parallel to the x-coordinate direction. Thus, to scan primary ion beam 116 in a direction parallel to the x-coordinate direction in an exposure pattern, controller 114 adjusts the electrical potentials applied to the first pair of deflection electrodes.

Similarly, by adjusting the electrical potentials applied to the second pair of deflection electrodes, 410a and 410b, a component of the resulting deflection of primary ion beam 116 is parallel to the y-coordinate direction. Accordingly, to scan primary ion beam 116 in a direction parallel to the y-coordinate direction in an exposure pattern, controller 114 adjusts the electrical potentials applied to the second pair of deflection electrodes.

To prevent primary ion beam 116 from being incident on sample 150, controller 114 can adjust the electrical potentials applied to either or both pairs of deflection electrodes to cause primary ion beam 116 to be intercepted by a beam blocking element. For example, by applying suitable electrical potentials to electrodes 410a and 410b, primary ion beam 116 can be deflected such that the beam is blocked by beam blocking elements 512 in ion beam optics 104. Beam blocking elements can also be positioned external to ion beam optics 104, and the electrical potentials applied to deflection electrodes adjusted to steer primary ion beam 116 to be incident on the external beam blocking elements.

After mass spectral information about the sample has been acquired by scanning primary ion beam 116 across the sample according to an exposure pattern and measuring secondary ions 118a generated from the sample, the mass spectral information can be used by controller 114 to form one or more images of the sample. An image formed in this manner can be analyzed to identify the boundaries of individual cells, and/or subcellular features in individual cells, in the image. A variety of methods can be used to identify cell boundaries using techniques such as image segmentation, as described generally for example in Ko et al., *J. Digital Imaging* 22: 259-74 (2009), and Ong, *Comput. Biol. Med.* 26: 269-79 (1996), the entire contents of which are incorporated herein by reference. Examples of computational techniques for image segmentation that can be used include, but are not limited to, thresholding techniques (as described for example in Korde, et al., *Anal. Quant. Cytol. Histol.* 31: 83-89 (2009), and Tuominen et al., *Breast Cancer Res.* 12, R56 (2010)), adaptive attention windows (as described for example in Ko et al. cited above), and gradient flow tracking (as described for example in Li et al., *J. Microscopy* 231: 47-58 (2008)). The entire contents of each of the foregoing references is incorporated by reference herein.

Once individual cells have been identified, measured secondary ion signals that correspond to each individual cell (or subcellular features thereof) can be further processed to determine information about the sample on a per-cell basis. For example, signals corresponding to individual cells can be integrated to yield information about the quantitative amount of each mass tag of interest within each cell. In this manner, abundances of different antigens, nucleic acids, and other biological entities of interest within each cell to which mass tags are bound can be quantitatively determined.

Determining the amount of each mass tag associated with each cell can permit classification of the cells in the sample. That is, individual cells and/or subcellular features can be assigned to one or more classes based on the types and/or quantities of mass tags that are bound to the cells/subcellular features. This information can be used by controller 114 to generate one or more output images in which the classifications of various cells and/or subcellular features are displayed, e.g., via output display 240, to a system user.

For example, controller 114 can generate a false-color image in which cells and/or subcellular features are color-coded according to the types and quantities of mass tags bound to the cells. The intensities of the colors of each pixel in the image can correlate with the magnitude of the signal obtained for the corresponding location on the sample. In other words, the intensity of the color in any single pixel of the cell image can be correlated with the amount of one or more specific mass tags that are bound to the sample at the corresponding sample location.

In some embodiments, MIBI techniques can be used to selectively obtain information about a relatively thin outer layer of the sample, because secondary ions 118a are generated from the sample primarily from the thin outer later. For example, in certain embodiments, secondary ion generation (and therefore information determination) occurs within a sample thickness of 1.0 micron or less (e.g., 500 nm or less, 200 nm or less, 100 nm or less, 50 nm or less, 20 nm or less, 10 nm or less, 5 nm or less, 2 nm or less, 1 nm or less).

Further, in general, the dose of primary ions to which the sample is exposed is relatively small, so that organic compounds present in the sample can be ionized while maintaining their chemical structure, allowing organic compounds to be analyzed (e.g., identified from the mass spectral information) without undergoing significant degradation. Reducing sample degradation can reduce background noise in the resulting spectral data that would otherwise be present due to spurious signals from degradation fragments of the organic compounds.

C. Sample Preparation and Mass Tags

MIBI relies on using a focused ion beam to release secondary ions from a sample specifically labeled with one or more different types of mass tags. "Labeling" refers to processes by which detectable moieties ("labels") are attached to structures of interest within a sample. Such structures, which can include various cellular components (e.g., cell walls, cytoplasm, nuclei, nuclear membranes, mitochondria) and biological structures and biochemical entities within biological samples (e.g., antigens, antibodies, proteins, peptides, nucleic acids, enzymes, enzymatic receptors) are referred to collectively herein as "analytes". By attaching labels to analytes, the presence of the analytes in the sample can be determined and quantified by detecting the corresponding bound labels.

The detectable moieties or labels generally include a mass tag and as well as a binding reagent. "Specific labeling" or "specific binding" refers to a strong, relatively exclusive, and preferential attachment of a binding reagent to an analyte, in contrast to non-specific binding in which a binding reagent attaches to many different portions (cellular components and/or biochemical structures and/or biochemical entities) of the sample. For example, antigen-antibody binding is an example of specific binding. Where an antigen (the analyte) is located in a sample, a binding reagent that includes a complementary antibody preferentially binds to the analyte antigen. A mass tag that is bound to the antibody is also therefore preferentially attached to the analyte antigen.

Specific binding can refer to an interaction that discriminates between desirable (targeted) and undesirable analytes (e.g., antigens 502) in a sample, in some embodiments more than about 10 to 100-fold or more (e.g., more than about 1000- or 10,000-fold). In certain embodiments, the affinity between a binding reagent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-11}$ M, or less than about $10^{-12}$ M or less.

Antigens and complementary, specific-binding antibodies will be discussed by way of example in this section. However, it should be understood that the systems and methods disclosed herein are not limited to the attachment of mass tags via antigen-antibody binding. A variety of other specific binding reagents can also be used, including aptamers (that specifically bind to nucleic acids), chromogenic stains, and/or other chemical agents By way of example, in some embodiments, the stain can be one or more of phalloidin, gadodiamide, acridine orange, bismarck brown, barmine, Coomassie blue, is bresyl violet, brystal violet, DAPI, hematoxylin, eosin, ethidium bromide, acid fuchsine, haematoxylin, hoechst stains, iodine, malachite green, methyl green, methylene blue, neutral red, Nile blue, Nile red, osmium tetroxide (formal name: osmium tetraoxide), rhodamine, safranin, phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, vanadyl sulfate, or any derivative thereof. The stain can be specific for any feature of interest, such as a protein or class of proteins, phospholipids, DNA (e.g., dsDNA, ssDNA), RNA, an organelle (e.g., cell membrane, mitochondria, endoplasmic recticulum, golg body, nulear envelope, and so forth), a compartment of the cell (e.g., cytosol, nuclear fraction, and so forth). The stain can additionally be used to enhance contrast or imaging of intracellular or extracellular structures.

In certain embodiments, the stain can be suitable for administration to a live subject. The stain may be administered to the subject by any suitable means, such as ingestion, injection (e.g., into the blood circulation), or topical administration (e.g., during a surgery). Such a stain may be specific for a tissue, biological structure (e.g., blood vessel, lesion), or cell type of interest. The stain can be incorporated into cells of the subject of a cellular process, such as glucose uptake. Examples of such stains include, without limitation, gadolinium, cisplatin, halogenated carbohydrates (e.g., carbohydrates which are fluorinated, chlorinated, brominated, iodinated), and so forth. Other injectable stains used in imaging techniques (e.g., such as MRI, PET scans, CT scans and so forth) can be conjugated to a mass tag if not inherently associated with a mass tag, and administered to a live subject. A sample may be obtained from the subject after administration, for use in the methods described herein.

Figure 5:
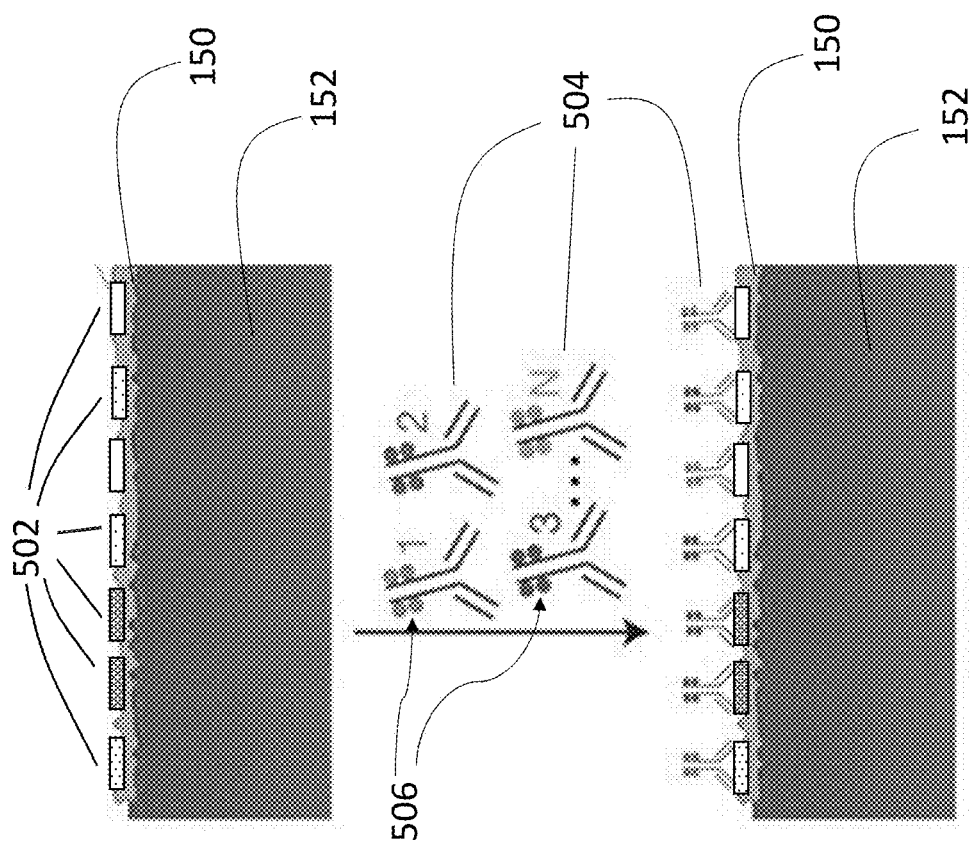
FIG. 5 is a schematic cross-sectional diagram of a sample labeled with mass tags.

As discussed above, mass tags are bound to binding reagents and are attached to analytes when the binding reagents bind to the analytes. As used herein "mass tags" are detectable moieties that are identifiable by their atomic mass and/or mass spectral profile FIG. 5 is a schematic cross-sectional diagram of sample 150 on substrate 152. Sample 150 contains proteins expressing a number of different antigens 502. Antibodies 504 are labeled with mass tags 506 unique for each antibody type. The tagged antibodies 504 specifically bind to corresponding antigens 502 on the surface of sample 150. Mass tags 506 are released as secondary ions from sample 150 when the sample is exposed to focused ion beam 116. Tags 506 are collected and analyzed to identify and quantify the presence of antigens 502 that correspond to released mass tags 506 in the scanned portion of sample 150.

Examples of antigens 502 that can be targeted include, but are not limited to, carcinoembryonic antigen (for identification of adenocarcinomas, cytokeratins (for identification of carcinomas but may also be expressed in some sarcomas), CD15 and CD30 (for Hodgkin's disease), alpha fetoprotein (for yolk sac tumors and hepatocellular carcinoma), CD 117 (for gastrointestinal stromal tumors), CD 10 (for renal cell carcinoma and acute lymphoblastic leukemia), prostate specific antigen (for prostate cancer), estrogens and progesterone (for tumour identification), CD20 (for identification of β-cell lymphomas) and CD3 (for identification of T-cell lymphomas).

Examples of antibodies 504 include, but are not limited to, the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOR-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids). Antibodies 504 can also generally include antibodies or immunoglobulins of any isotype, fragments of antibodies which retain specific binding to antigen, including, but not limited to, Fab, Fv, scFv, and Fd fragments, chimeric antibodies, humanized antibodies, minibodies, single-chain antibodies, and fusion proteins comprising an antigen-binding portion of an antibody and a non-antibody protein. Also encompassed by the term "antibody" are Fab', Fv, F(ab')$_2$, and or other antibody fragments that retain specific binding to antigen and monoclonal antibodies. Antibodies may exist in a variety of other forms including, for example, Fv, Fab, and (Fab')$_2$, as well as bi-functional (i.e. bi-specific) hybrid antibodies and in single chains.

Mass tag 506 may have a mass in the range of 21 to 238 atomic mass units. There are greater than 100 non-biological stable isotopes of elements between 21 and 238 AMU that can be simultaneously measured via MIBI without significant overlap. Examples of stable isotopes used in mass tags include isotopes of transition metals, post transition metals, halides, noble metals, or lanthanides, or any other element not commonly found in the sample under analysis. These may include, but are not limited to the high molecular weight members of the transition metals (e.g. Rh, Ir, Cd, Au), post-transition metals (e.g. Al, Ga, In, Tl), metalloids (e.g. Te, Bi), alkaline metals, halogens, and actinides. Mass tag 506 could also consist of lower molecular weight transition elements not common in biological matrices (e.g. Al, W, and Hg). In some embodiments, tagging isotopes may comprise non-lanthanide elements that can form stable metal chelator tags for the applications described herein.

As noted above, in certain embodiments, mass tag 506 can include one or more lanthanide elements. Lanthanide elements, which have atomic numbers between 58 and 71, are sometimes referred to as "rare earth metals." Examples of lanthanide elements that can be used in mass tag 506 include lanthanum, cerium, praseodymium, neodymium, samarium, europium, gadolinium, terbium, dysprosium, holmium, erbium, thulium, ytterbium, and lutetium.

Lanthanide elements can be particularly useful as mass tags for several reasons. Such elements typically have natural abundances in living tissue that are very low, and therefore detected signals arising from ions of such elements can generally be regarded as due to specific labeling of the tissue, and not due to naturally occurring concentrations of such elements. In addition, lanthanide elements have well defined masses, and measured signals arising from the ions of such elements can readily be recognized against background noise contributions. Further, lanthanide elements do not undergo fragmentation, degradation, or other physical or chemical processes that would otherwise generate a multiplicity of ion signals and/or reduce the amplitude of the molecular ion peak. Further still, due to absence of such degradation pathways, ions originating from lanthanide elements can be "collected" following generation, effectively increasing the integration or signal averaging time during measurement of ion currents, without leading to loss of signal due to collisional and/or spontaneous fragmentation.

As discussed above, in some embodiments, mass tag 506 can include one or more noble metal atoms. Suitable examples of noble metals include, but are not limited to, palladium, silver, iridium, platinum and gold.

In certain embodiments, mass tags 506 can include a chelating ligand (e.g., a chelating polymer made up of repeating units of a metal chelator), such as ethylenediaminetetraacetic acid (EDTA) or diethylene triamine pentaacetic acid (DTPA), chelating one or more atoms of a single non-biological isotope (e.g., lanthanides). The chelating ligand can be used to selectively change the mass of certain mass tags (e.g., by binding to specific lanthanides), thereby adjusting the detection window (i.e., the range of values of the mass-to-charge ratio (m/z) over which the mass tags are detected). In this manner, the mass tags can be selectively detected within a detection window that is less "crowded" with contributions from other background species. Alternatively, or in addition, signals from certain mass tags can be "compressed" into a particular detection window, leading to a smaller range of m/z ratios that are scanned and thereby reducing the overall measurement time.

In some embodiments, optical staining methods can be combined with mass tagging to achieve multiplexed measurement of features of interest within a sample. This combination of techniques can allow some areas of the sample be distinguished via optical methods, and other areas to be distinguished via mass spectral information. For example, in certain embodiments, a certain type of mass tag can be located in multiple different cells and/or cell compartments. As such, it can be difficult to unambiguously assign secondary ion signals arising from the mass tags to specific cells/compartments.

However, if the sample is also stained with one or more chromogenic and/or fluorescent stains that differentially label the sample, secondary ion signals can be assigned to specific cells/compartments based on the localization of the stains within the sample, as determined from optical measurements of the sample. In this manner, signals arising from a common type of secondary ion (e.g., a common type of mass tag) can be localized within different regions of a sample. As an example, consider a sample to which a mass tag has been applied, and which is also stained with a Her2 membrane stain and an ER nuclear stain. Secondary ion signals arising from the mass tag (e.g., a lanthanide metal-based tag) can be assigned to different cellular compartments within individual sample cells based on their co-localization with optical absorption/emission signals arising from the Her2 and ER stains.

Alternatively, in certain embodiments, spatially resolved secondary ion signals attributable to different mass tags can be used to distinguish among regions of a sample where two or more chromogenic and/or fluorescent stains co-localize. As an example, consider a sample stained with an ER nuclear stain and a dsDNA or histone H3 stain (both of which co-localize with the ER stain in the sample). If different regions within the sample where these co-localized stains are located are also differentially labeled with mass tags, the secondary ion signals arising from the mass tags can be used to assign the ER and dsDNA/histone H3 signals to the different regions.

In some embodiments, additional structural moieties can be present as intermediate structures between mass tags and specific binding reagents. Such structural moieties can function as linking members that facilitate the attachment of mass tags to specific binding reagents. In particular, these structural moieties can permit preparation of wide range of different mass tag-specific binding reagent adducts using a general preparative scheme rather than using specialized synthetic methods for each different type of adduct.

In general, mass tag 506 (MT) can be bound or conjugated to a reactive group (R) which in turn is bound or conjugated to a specific binding reagent (SBR) such as an antibody. The structure of such an adduct can be represented as MT-R-SBR, with the mass tag and reactive group forming intermediate compound R-T. Further, in certain embodiments, a spacer moiety (S) can be present between the reactive group and the mass tag so that the structure of the adduct can be represented as MT-S-R-SBR.

In some embodiments, for example, R can be a maleimide or halogen-containing group that is sulfhydryl reactive, an N-hydroxysuccinimide (NHS)-carbonate that is amine-reactive, and/or an N,N-diisopropyl-2-cyanoethyl phosphoramidite that is hydroxyl-reactive. Such reactive groups can react with other groups on the specific binding reagent, e.g., a cysteine or other residue of an antibody, or a sulfhydryl group of an oligonucleotide.

In certain embodiments, MT can be a polymer of, e.g., 10-500 units, where each unit of the polymer contains a coordinated transition metal atom. Suitable examples of reactive groups R and mass tags MT containing coordinating groups, including DOTA and DTPA-based polychetants, are described in Manabe et al., *Biochim. Biophys. Acta* 883: 430-467 (1986), and in U.S. Pat. Nos. 6,203,775, 5,364,314, the entire contents of each of which are incorporated herein by reference.

Additional examples of mass tags MT and reactive groups R are described in U.S. Patent Application Publication No. US 2008/0003316, and in U.S. Pat. Nos. 6,203,775, 7,267, 994, 6,274,713, and 5,364,313, the entire contents of each of which are incorporated herein by reference. Methods for making polymer-based mass tags are also described in Zhang et al., Agnew. Chem. Int. Ed. 46: 3111-3114 (2007), the entire contents of which are incorporated herein by reference.

A variety of different chelating agents/moieties can also be used to coordinate to and bind metal ions in mass tags. Examples of such chelating agents/moieties include, but are not limited to, EDTA, EGTA, and Heme. In general, chelating agents/moieties can bind metal ions bearing single, double, triple, and quadruple charges. Methods for linking such agents/moieties to specific binding reagents are known in the art.

Examples of samples 150 that can be analyzed with MIBI include bulk tissues extracted from a human or animal patient (e.g., tumor tissue excised during biopsy, or another type of tissue sample retrieved via another invasive surgical or non-invasive procedure), cell populations (e.g., blood cells), or organelles within individual cells. As an example, in some embodiments, sample 150 corresponds to a formalin-fixed, paraffin-embedded tissue sample. Such samples can be prepared during histological workup of biopsied tissue from cancer tumors and other anatomical structures.

Biological structures and components that can be examined include cell walls, nuclei, cytoplasm, membrane, keratin, muscle fibers, collagen, bone, proteins, nucleic acid, and other types of cellular macromolecules (e.g., carbohydrates, lipids). MIBI can be used in a variety of ways, from highlighting muscle fibers or connective tissue in tissue samples to classifying different blood cells in cell samples.

Figure 6:
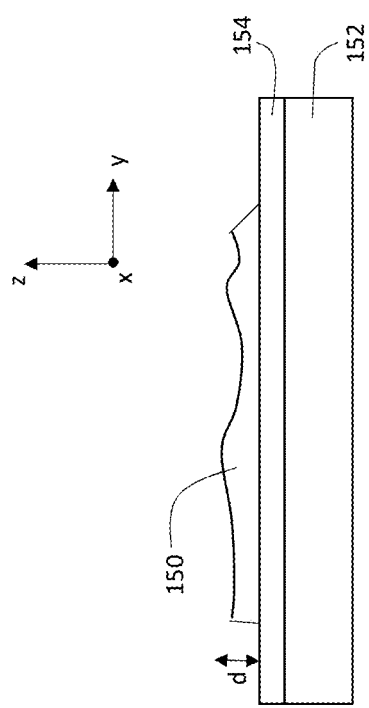
FIG. 6 is a schematic cross-sectional diagram of a tissue section sample positioned on a substrate.

FIG. 6 is a schematic cross-sectional diagram of a tissue sample 150 on substrate 152. Positioned between substrate 152 and sample 150 in FIG. 6 is an optional coating 154. Coating 154 can prevent charging of the sample, which can lead to disruption of the primary ion beam and, in some circumstances, perturb the process of secondary ion generation from the sample. When present, coating 154 can be electrically connected to voltage source 108 via electrodes 108a and 108b, as shown in FIG. 1.

Substrate 152 can be implemented as a microscope slide or another planar support structure, and can be formed from a variety of materials including various types of glass, plastics, silicon, and metals. In one example, silicon wafers (available from Silicon Valley Microelectronics, Santa Clara, Calif.) diced into 18 mm² pieces function as substrate 152. The wafers can be rinsed two times with methanol and polished with a cotton-tipped applicator. Cleaned wafer substrates are subsequently immersed in 2% poly-1-lysine solution (available from Sigma-Aldrich, St. Louis, Mo.) for 10 min and baked at 30° C. for 1 hr.

Coating 154, if present, can be formed of one or more metallic elements and/or one or more non-metallic compounds of relatively high conductivity. Examples of metallic elements used to form coating 154 include, but are not limited to, gold, tantalum, titanium, chromium, tin, and indium. In certain embodiments, coating 154 can be implemented as multiple distinct coating layers, each of which can be formed as a separate layer of a metallic element or a separate layer of a relatively high conductivity, non-metallic compound.

As shown in FIG. 6, sample 150 is approximately planar and extends in the x- and/or y-coordinate directions, and has a thickness d measured in the z-coordinate direction. Depending upon the method of preparation of sample 150, the sample can have an approximately constant thickness d across the planar extent of the sample parallel to the x-y coordinate plane. Alternatively, many real samples corresponding to excised tissue have non-constant thicknesses d across the planar extent of the sample parallel to the x-y coordinate plane. In FIG. 6, sample 150—which is shown in cross-section—has a non-constant thickness d measured in the z-coordinate direction.

In general, the thickness d of sample 150 depends upon the method by which sample 150 is obtained and processed prior to mounting on substrate 152. Certain samples, for example, are microtome-sliced from larger blocks of tissue, and can have relatively constant thicknesses. As another example, certain samples are obtained directly via excision, and can have variable thicknesses. The thickness d of sample 150 can be from 500 nm to 500 microns (e.g., from 1 micron to 300 microns, from 5 microns to 200 microns, from 10 microns to 150 microns, from 25 microns to 100 microns).

In some embodiments, substrate 152 can also include one or more additional coating materials to facilitate adhesion of sample 150 to substrate 152. Where no coating 154 is present, the one or more additional coating materials can be applied directly to substrate 150, such that the additional coating materials form a layer positioned between sample 150 and substrate 152. Where coating 154 is present, the one or more additional coating materials can be applied atop coating 154, for example, such that the additional coating materials form a layer positioned between coating 154 and sample 150. Suitable additional coating materials to facilitate adhesion of sample 150 include, but are not limited to, poly-1-lysine.

In certain embodiments, sample 150 corresponds to an array of single cells on a substrate. The array can be naturally occurring, and correspond to a regularly occurring, ordered arrangement of cells in a tissue sample. Alternatively, the array of cells can be a product of sample preparation. That is, the sample can be prepared by manual or automated placement of individual cells on substrate 152 (e.g., in a series of wells or depressions formed in substrate 152) to form the cell array.

Figure 7:
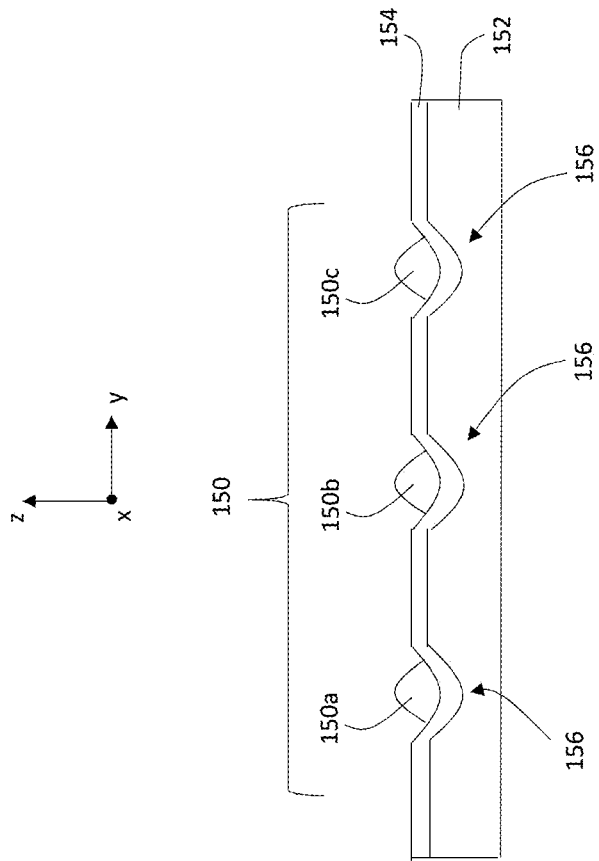
FIG. 7 is a schematic cross-sectional diagram of a sample with multiple cells positioned on a substrate.

FIG. 7 shows a schematic cross-sectional diagram of a cellular sample 150 positioned on a substrate 152. Substrate 152 optionally includes one or more conformal coating layers 154 as discussed above. In addition, substrate 152 includes an array of wells 156 corresponding to depressions formed in a surface of substrate 152. Each of the wells 156 contains a portion 150a-150c of sample 150. In general, while substrate 152 includes three wells 156 containing three separate portions 150a-150c of sample 150 in FIG. 7, more generally substrate 152 can include any number of wells 156, and sample 150 can be apportioned among any one or more of the wells 156.

Wells 156 (and the portions of sample 150 distributed among wells 156) can generally arranged in a variety of patterns in substrate 152. For example, wells 156 can form a linear (i.e., one dimensional) array in substrate 152. Alternatively, wells 156 can be distributed along one dimension in the plane of substrate 152, with irregular spacings between some or all of the wells.

As another example, wells 156 can form a two-dimensional array in substrate 152, with regular spacings between adjacent wells in directions parallel to both the x- and y-coordinate directions in the plane of substrate 152. Alternatively, in either or both of the directions parallel to the x- and y-coordinate directions in the plane of substrate 152, at least some of wells 156 can be spaced irregularly.

Where wells 156 form a two-dimensional array in substrate 152, the array can take a variety of forms. In some embodiments, the array of wells 156 can be a square or rectangular array. In certain embodiments, the array can be a hexagonal array, a polar array having radial symmetry, or another type of array having geometrical symmetry in plane of substrate 152.

As discussed above, each of the portions 150a-150c of sample 150 can include one or more cells. During sample preparation, each portion 150a-150c can be dispensed or positioned in a corresponding well 156 of substrate 152 to form sample 150. For example, each portion 150a-150c of sample 150 can be dispensed into a corresponding well 156 as a suspension of cells in a liquid medium, and the liquid medium subsequently removed (e.g., by washing or heating) to leave the cells in each well 156.

In general, for any sample type 150, to facilitate various biochemical structural analyses of sample 150 such as protein expression, sample 150 can be labeled with one or more different types of mass tags. When sample 150 is exposed to primary ion beam 116, the mass tags are ionized and liberated from sample 150. The ionized mass tags correspond to secondary ions 118a and form secondary ion beam 118 emerging from sample 150. Analysis of the secondary ions 118a present in secondary ion beam 118 as a function of the location of incidence 124 of ion beam 116 on sample 150 by controller 114 can yield a wealth of information about the biochemical structure of sample 150 at each of the locations of incidence 124.

To apply mass tags 506 to sample 150, each of the mass tags can be conjugated to a specific antibody 504 that selectively binds to an antigen receptor 502 in sample 150. For example, solutions of each of the antibody-conjugated mass tags can be prepared, and then sample 150 can be labeled by exposing sample 150 to each of the mass tag solutions. In some embodiments, sample 150 is exposed to multiple mass tag solutions sequentially and/or in parallel so that sample 150 can be labelled with multiple, distinct mass tags.

To prepare suitable mass tag labeling solutions, various methods can be used. In certain embodiments, for example, solutions are prepared by following a sequence of three steps: loading of a polymer linking moiety with a mass tagging element (e.g., a lanthanide metal element), reduction of an antibody, and conjugation of the metal-loaded polymer to the antibody. In the first step, for example, a metal-chelating polymer is loaded with a specific metal element.

To perform this step, the polymer can be suspended in Buffer 1 (available from IONpath, Menlo Park, Calif.), and the metal element of interest added. The mixture can then be incubated for 45 minutes at 37° C., and subsequently transferred to a filter (e.g., a 3 kDa molecular-weight cut off (MWCO) Amicon® spin filter, available from MilliporeSigma, Burlington, Mass.) that retains the polymer and enables removal of unbound metal tags by washing the polymer twice with Buffer 1.

The second step, which can be performed in parallel with the first step, is to prepare the antibody to receive the polymer. The antibody can be transferred to a filter (e.g., a 50 kDa MWCO Amicon® spin filter) that retains the antibody, and then washed twice with Buffer 2 (available from IONpath, Menlo Park, Calif.). Next, the antibody can be incubated with a reducing agent, such as 4 mM tris(2-carboxyethyl)phosphine (TCEP) for 30 minutes at 37° C. to partially reduce the antibody and expose sulfhydryl residues for conjugation with the maleimide-containing polymer. Following the incubation, the antibody can be washed twice with Buffer 3 (available from IONpath, Menlo Park, Calif.) using the same 50 kDa MWCO filter to remove the TCEP and prevent further reduction to the antibody.

In the third step, the metal-tagged polymer and reduced antibody can be combined and incubated for 60-90 minutes at 37° C. to conjugate the polymer to the antibody. Following this incubation, the mixture can be washed three times with Buffer 4 (available from IONpath, Menlo Park, Calif.) using the same 50 kDa MWCO filter, which retains the conjugated antibody and allows removal of unbound polymer. The concentration of the metal-tagged antibody can be determined by measuring optical absorbance at 280 nm (e.g., using a NanoDrop spectrofluorometer, available from ThermoFisher Scientific, Waltham, Mass.) for a solution of the metal-tagged antibody in Buffer 5 (available from IONpath, Menlo Park, Calif.), diluted to a concentration of between 200 µg/mL and 500 µg/mL, and stored at a temperature of 4° C.

In some embodiments, for preparation of samples consisting of arrays of cells, as shown in FIG. 7, cells in suspension can be augmented with surface marker antibodies and incubated at room temperature for approximately 30 minutes. Following incubation, cells can be washed twice with the mass tag labeling solutions to label the cells. Individual aliquots of the labeled cells, diluted in PBS to yield a desired concentration of cells per unit volume (e.g., approximately $10^7$ cells/mL), can then be placed in wells 156 and allowed to adhere for approximately 20 minutes. The adhered cells can then be gently rinsed with PBS, fixed for approximately 5 minutes in PBS with 2% glutaraldehyde, and rinsed twice with deionized water. After rinsing, samples can be dehydrated via a graded ethanol series, air dried at room temperature, and stored in a vacuum dessicator for at least 24 hours prior to analysis.

In some embodiments, for preparation of intact tissue samples, as shown in FIG. 6, such as samples obtained from biopsy, tissue samples can be mounted on substrate 152. Following mounting, the samples can be baked at approximately 65° C. for 15 minutes, deparaffinized in xylene (if obtained from FFPE tissue blocks), and rehydrated via a graded ethanol series. The samples can then be immersed in epitope retrieval buffer (10 mM sodium citrate, pH 6) and placed in a pressure cooker (available from Electron Microscopy Sciences, Hatfield, Pa.) for approximately 30 minutes. Subsequently, the samples can be rinsed twice with deionized water and once with wash buffer (TBS, 0.1% Tween, pH 7.2). Residual buffer solution can be removed by gently touching the samples with a lint free tissue. In some embodiments, the samples can then incubated with blocking buffer for approximately 30 minutes (TBS, 0.1% Tween, 3% BSA, 10% donkey serum, pH 7.2).

In some embodiments, the blocking buffer can be subsequently removed and the samples labeled overnight with the mass tag labeling solutions at 4° C. in a humidified chamber. Following labeling, the samples can then be rinsed twice in wash buffer, postfixed for approximately 5 minutes (PBS, 2% glutaraldehyde), rinsed in deionized water, and stained with Harris hematoxylin for 10 seconds. In some embodiments, the samples are dehydrated after rinsing via graded ethanol series, air dried at room temperature, and stored in a vacuum dessicator for at least 24 hours prior to analysis.

For example, a breast tumor tissue section can be prepared for MIBI imaging as follows. Tissue sections (e.g., of 4 µm thickness) can be cut from formalin-fixed, paraffin-embedded ("FFPE") tissue blocks of human breast tumor using a microtome, mounted on poly-1-lysine-coated silicon substrate for MIBI analysis. In some embodiments, silicon-mounted sections can subsequently be baked at 65° C. for 15 min, deparaffinized in xylene, and rehydrated via a graded ethanol series. The sections can then be immersed in epitope retrieval buffer (10 mM sodium citrate, pH 6) and placed in a pressure cooker for 30 min (e.g., from Electron Microscopy Sciences, Hatfield, Pa.). In some embodiments, after the pressure cooker, the sections can be rinsed twice with $dH_2O$ and once with wash buffer (e.g., buffer containing Tris-buffered saline ("TBS"), 0.1% Tween, pH 7.2). Residual buffer can be removed, for example, by gently touching the surface with a lint-free tissue. The sections can then be incubated with blocking buffer for 30 min (TBS, 0.1% Tween, 3% BSA, 10% donkey serum, pH 7.2). The sections can be rinsed twice in wash buffer, postfixed for 5 min (PBS, 2% glutaraldehyde), rinsed in $dH_2O$. Finally, the sections can be dehydrated via graded ethanol series, air dried at room temperature, and then stored in a vacuum desiccator for at least 24 hrs prior to imaging.

Antigen retrieval can be performed using a decloaking chamber (e.g., from Biocare Medical, Concord, Calif.) with citrate buffer at pH 6.0, 125° C. and pressure to 15 psi. Sections can be in the chamber for a total time of 45 min. Incubations with primary antibodies can be performed at room temperature overnight in a humidified chamber. Normal goat serum can be used for blocking. Biotinylated goat anti-rabbit (1:1000) can be the secondary antibody used with a Vectastain ABC Kit Elite. A Peroxidase Substrate Kit DAB (e.g., from Vector Labs, Burlingame, Calif.) can be used for amplification and visualization of signal, respectively. Tissues known to contain each assessed antigen can be used as positive controls.

It should be understood that the above preparative steps are merely provided as examples of methods for sample preparation, and that modifications to the above sequences of steps also yield samples that are suitably labeled with mass tags and prepared for MIBI analysis. In particular, modifications to be above sequences of preparative steps can be undertaken based on the nature of the samples (e.g., the type of tissue to which the samples correspond).

D. Ion Optics

Figure 8:
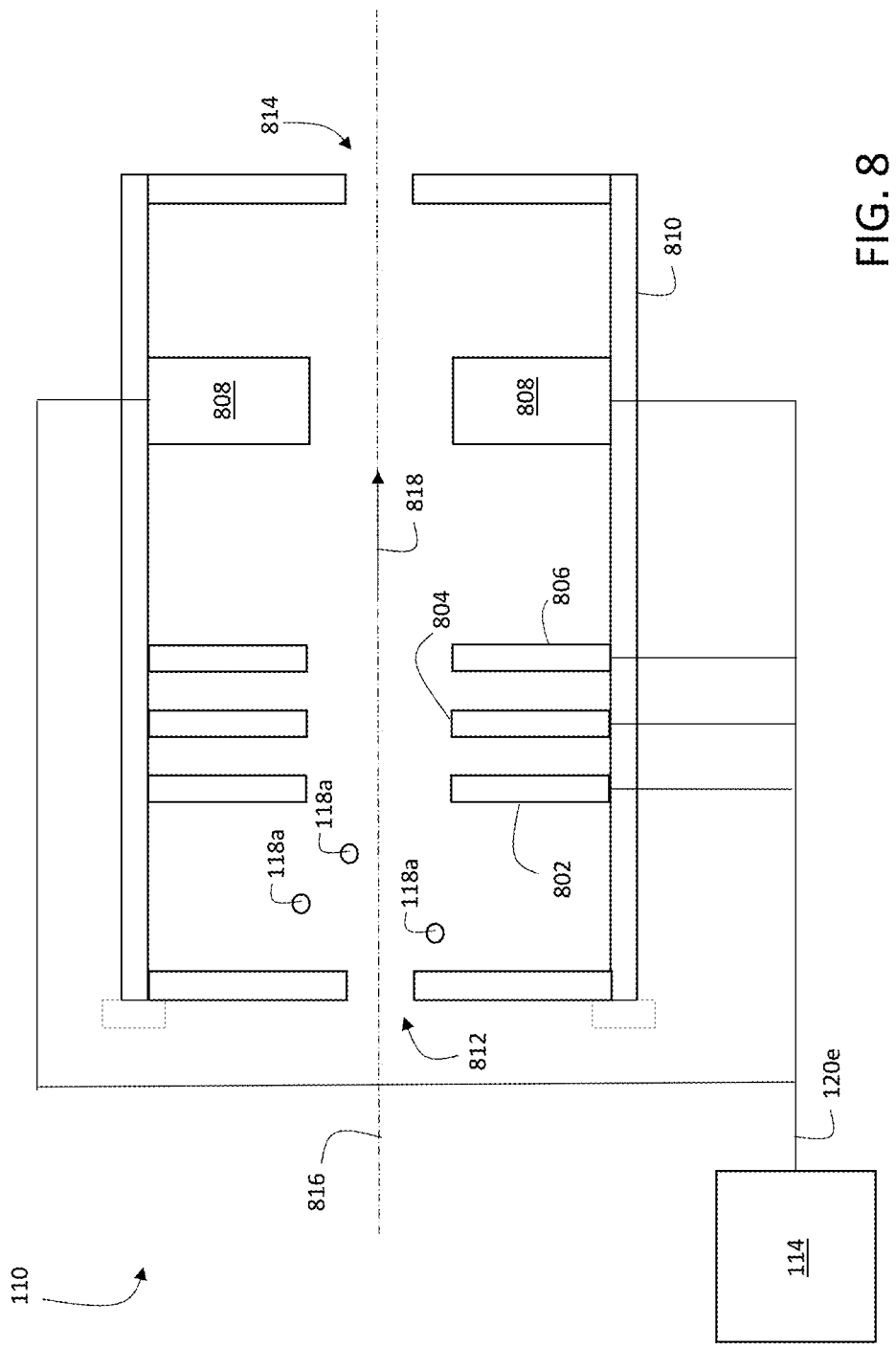
FIG. 8 is a schematic diagram showing an example of a portion of ion optics.

Returning to FIG. 1, system 100 includes ion optics 110 which function to guide secondary ions 118*a* from sample chamber 126 into detection apparatus 112. In general, ion optics 110 can include a wide variety of different ion optical elements for purposes of guiding secondary ions 118*a*. FIG. 8 is a schematic diagram showing an embodiment of ion optics 110. Ion optics 110 in FIG. 8 include a housing 810 featuring an entrance aperture 812 and an exit aperture 814. During operation, secondary ions 118*a* enter ion optics 110 through entrance aperture 812 from sample chamber 126 and propagate generally in direction 818 along central axis 816 toward exit aperture 814. Secondary ions 118*a* exit through aperture 814 and enter detection apparatus 112.

Ion optics 110 can include a variety of different ion optical elements for directing secondary ions 118 and adjusting the properties of the ions. In some embodiments, as shown in FIG. 8, ion optics 110 include one or more focusing elements 802, 804, and 806, which are connected to controller 114 via signal line 120*e*. Ion optics 110 also include beam deflecting elements 808 connected to controller 114 via signal line 120*e*. During operation of system 100, secondary ions 118*a* generated in chamber 126 enter ion optics 110 through aperture 812 and propagate generally along direction 818. Controller 114 adjusts electrical potentials applied to focusing elements 802, 804, 806 and to beam deflecting elements 808 to ensure that direction 818 is approximately parallel to axis 816. In addition, but adjusting the potentials applied to the focusing and beam deflecting elements, controller 114 adjusts the diameter of the beam of secondary ions 118*a* and the trajectory of the secondary ions 118*a* as they exit ion optics 110 through aperture 814.

In some embodiments, in addition to or as an alternative to the elements shown in FIG. 8, ion optics 110 can include one or more ion traps. Ion traps can be used to temporarily "collect" or concentrate secondary ions 118*a* produced in chamber 126 before they pass on to detection apparatus 112.

Figure 9:
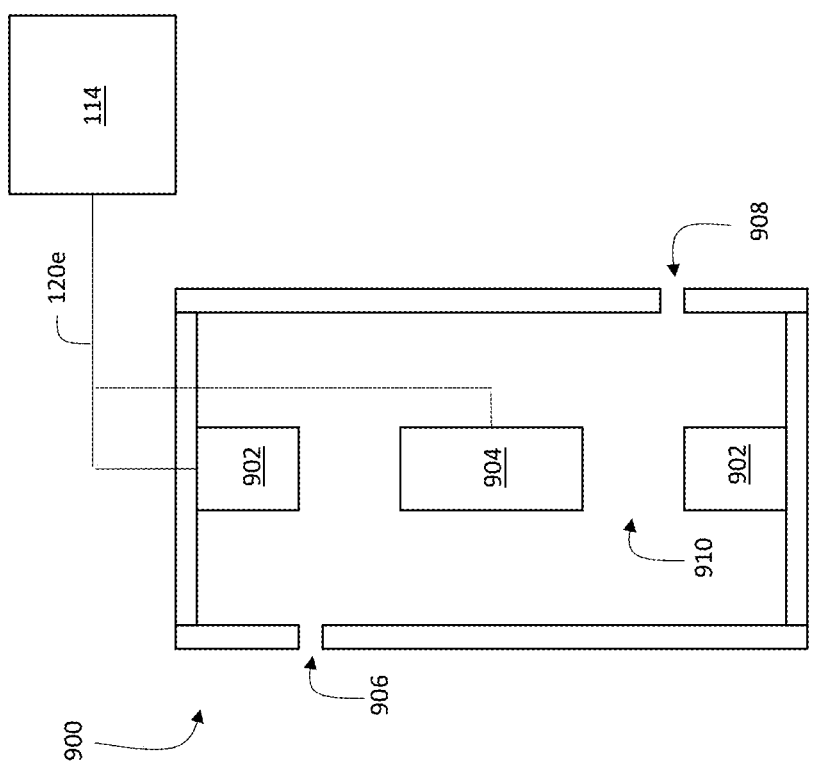
FIG. 9 is a schematic diagram showing an example of an ion trap.

A wide variety of different types of ion traps can be used in ion optics 110, and the choice of ion trap can depend upon a variety of factors such as the yield of secondary ions 118*a*. For example, in some embodiments, ion optics 110 can include a toroidal ion trap. FIG. 9 is a schematic diagram of a toroidal ion trap 900 that includes electrodes 902 and 904 connected to controller 114 via signal line 120*e*. During operation of ion trap 900, secondary ions 118*a* enter the trap through aperture 906. Controller 114 adjusts electrical potentials applied to electrodes 902 and 904 so that a toroidal trapping force is applied by the electrodes to secondary ions 118*a*, causing the secondary ions to undergo precessional motion within the gap 910 between electrodes 902 and 904. The potentials applied to electrodes 902 and 904 can be swept such that after the secondary ions 118*a* are trapped within the toroidal gap 910, secondary ions 118*a* of particular m/z ratios are selectively ejected from trap 900 through aperture 908. In this manner, the trapped ions can be directed to detection apparatus 112 according to their m/z ratio, such that detection apparatus 112 can detect secondary ions at high resolution. Other features and aspects of toroidal ion traps are disclosed, for example, in Lammert et al., "Miniature Toroidal Radio Frequency Ion Trap Mass Analyzer," *J. Am. Soc. Mass Spectrom.* 17: 916-922 (2006), and in Austin et al., "Halo Ion Trap Mass Spectrometer," *Anal. Chem.* 79: 2927-2932 (2007), the entire contents of each of which are incorporated herein by reference.

Figure 10:
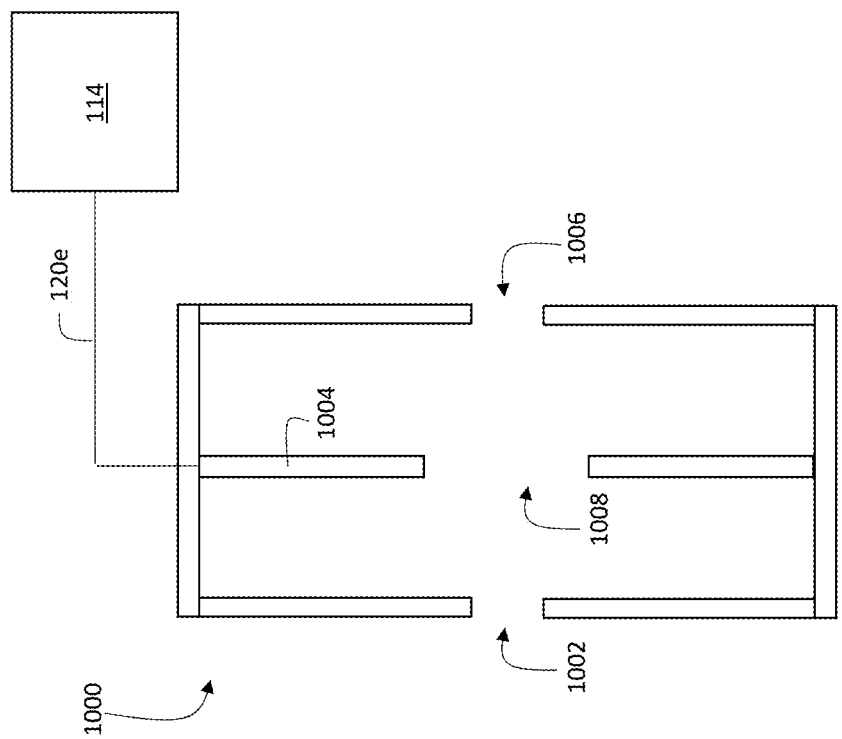
FIG. 10 is a schematic diagram showing another example of an ion trap.

As another example, in some embodiments, ion optics 110 can include a radial ion trap. FIG. 10 shows a schematic diagram of a radial ion trap 1000 that includes an entrance aperture 1002, an exit aperture 1006, and one or more trapping electrodes 1004 connected to controller 114 via signal line 120*e*. During operation, secondary ions 118*a* enter trap 1000 through aperture 1002. Controller 114 applies electrical potentials to the one or more trapping electrodes 1004, generating a radial trapping field within ion trap 1000 that causes secondary ions 118*a* to undergo precessional motion within trapping region 1008. Controller 114 varies the electrical potentials such that only secondary ions 118*a* with a selected range of m/z values remain trapped within region 1008. Secondary ions 118*a* that fall outside this range of m/z values are ejected through aperture 1006. By varying the electrical potentials, secondary ions with different m/z ratios can be selectively "swept" out of ion trap 1000 and into detection apparatus 112.

The shape of trapping region 1008 determines the nature of the trapping field generated by controller 114 in ion trap 1000. In certain embodiments, for example, trapping region 1008 corresponds to an elliptical aperture formed in electrode 1004, and ion trap 1000 is an elliptical ion trap with an elliptical trapping field. In some embodiments, trapping region 1008 corresponds to a circular aperture formed in electrode 1004, and ion trap 1000 is a circular ion trap with a circular trapping field. Other aspects and features of radial ion traps are disclosed, for example, in Patterson et al., "Miniature Cylindrical Ion Traps Mass Spectrometer," *Anal. Chem.* 74: 6145-6153 (2002), in Blain et al., "Towards the Hand-Held Mass Spectrometer: Design Considerations, Simulation, and Fabrication of Micrometer-Scaled Cylindrical Ion Traps," *Int. J. Mass Spectrom.* 236: 91-104 (2004), and in Riter et al., "Analytical Performance of a Miniature Cylindrical Ion Trap Mass Spectrometer," *Anal. Chem.* 74: 6154-6162 (2002), the entire contents of each of which are incorporated by reference herein.

The foregoing discussion provides a variety of examples of different elements that can be included in ion optics 110, but it should be understood that ion optics 110 can also include other elements as well. Further, in some embodiments, ion optics 110 may not include any elements. That is, secondary ions 118*a* can pass directly from chamber 126 to detection apparatus 112 without passing through or being manipulated by any elements that correspond to ion optics 110.

E. Detection Apparatus

After passing through ion optics 110, secondary ions 118*a* are detected by detection apparatus 112. Detection apparatus 112 can include a wide variety of different elements. In general, detection apparatus 112 functions to generate electrical signals (e.g., electrical voltages, electrical currents) that are qualitatively and/or quantitatively representative of secondary ion populations that enter detection apparatus 112.

In some embodiments, for example, detection apparatus 112 can include one or more Faraday cup detectors, which are connected to controller 114 via signal line 120*f*. When a secondary ion 118*a* is incident on a Faraday cup detector, the detector generates an electrical signal which is communicated to controller 114 via signal line 120*f*. When a suitable ion trap for m/z resolution is used in ion optics 110 as discussed above, signals generated by Faraday cup detectors can be measured by controller 114 as a function of m/z, thereby providing quantitative information about populations of secondary ions 118*a*.

Figure 11:
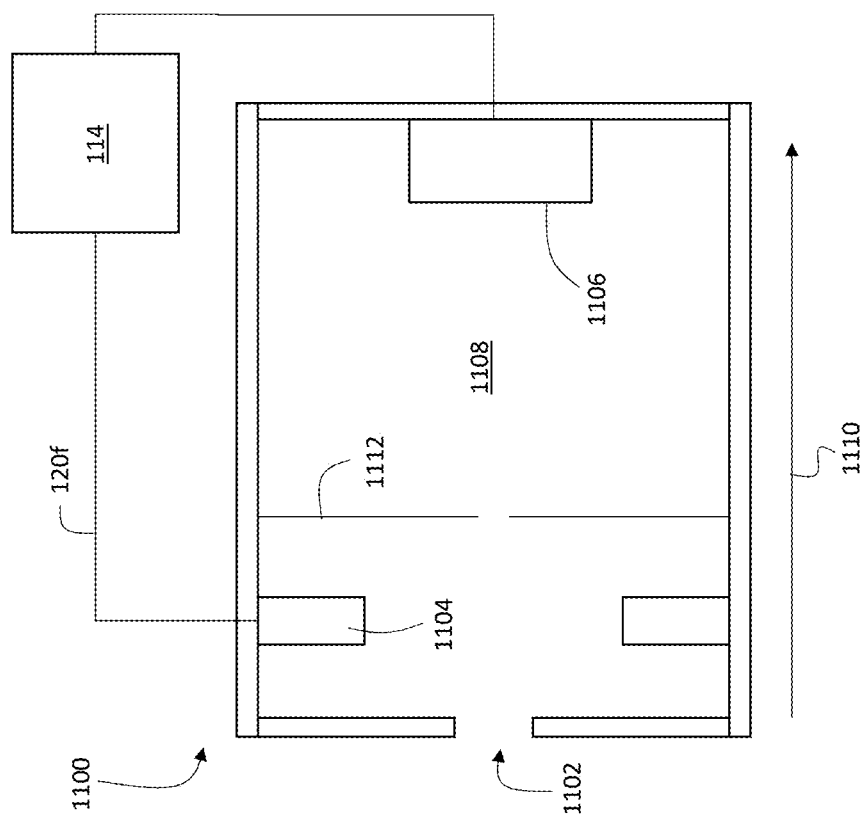
FIG. 11 is a schematic diagram showing an example of a linear time-of-flight detector.

In certain embodiments, detection apparatus 112 can include a linear time-of-flight (lin-TOF) detector. FIG. 11 is a schematic diagram showing an embodiment of a lin-TOF detector 1100. Detector 1100 optionally includes one or more electrodes 1104, and a detection element 1106 (such as a Faraday detector), connected to controller 114 via signal line 120*f*. During operation, secondary ions 118*a* enter detector 1100 via aperture 1102. The properties of the ions can optionally be adjusted (e.g., deflection and/or focusing of the secondary ions 118*a*) by controller 114 via application of suitable electrical potentials to electrodes 1104. Secondary ions 118a then propagate generally along direction 1110 toward detection element 1106, passing through a drift region 1108.

Secondary ions 118a of different masses propagate at different velocities. Accordingly, the elapsed time during which each secondary ion 118a traverses drift region 1108 is related to the ion's m/z ratio. Controller 114 measures electrical signals generated by detection element 1106 as a function of time, where the time associated with each signal is representative of a particular m/z ratio. Calibration information is used by controller 114 to convert ion arrival times at detection element 1106 into particular m/z ratios, such that ion populations as a function of m/z ratio can be quantitatively determined.

In a time-of-flight detector, the ion detection cycle is initiated at time zero. Because the m/z ratio associated with each signal is a direct function of the time at which the signal is measured relative to time zero, it is important that time zero be accurately and reproducibly established during each detection cycle. For a lin-TOF detector, time zero can be established different ways depending upon the manner in which secondary ions 118a are generated.

In some embodiments, ion source 102 generates a continuous primary ion beam 116 such that secondary ions 118a are continuously generated from sample 150. In such a case, time zero is defined by controller 114 at detector 1100. Prior to performing an ion detection cycle, controller 114 adjusts the electrical potential applied to electrode 1104 such that the secondary ions 118a entering aperture 1102 are deflected and blocked by aperture 1112, and do not reach detection element 1106. To initiate an ion detection cycle, controller 114 adjusts the electrical potential applied to electrode 1104 so that secondary ions 118a can propagate through detector 1100 and reach detection element 1106. The time at which controller 114 initiates the detection cycle by adjusting the electrical potential applied to electrode 1104 corresponds to time zero (t=0) in the detection cycle, and measurement times of ion signals generated by detection element 1106 are referenced to this time zero.

Typically, controller 114 initiates an ion detection cycle by adjusting the electrical potential applied to electrode 1104 for a relatively brief time period to allow a pulse or burst of secondary ions 118a to propagate to, and be detected by, detection element 1106. After admitting the pulse of secondary ions 118a, however, controller 114 readjusts the electrical potential applied to electrode 1104 such that while the admitted secondary ions 118a are detected, additional secondary ions 118a arriving at aperture 1112 are blocked.

Figure 12:
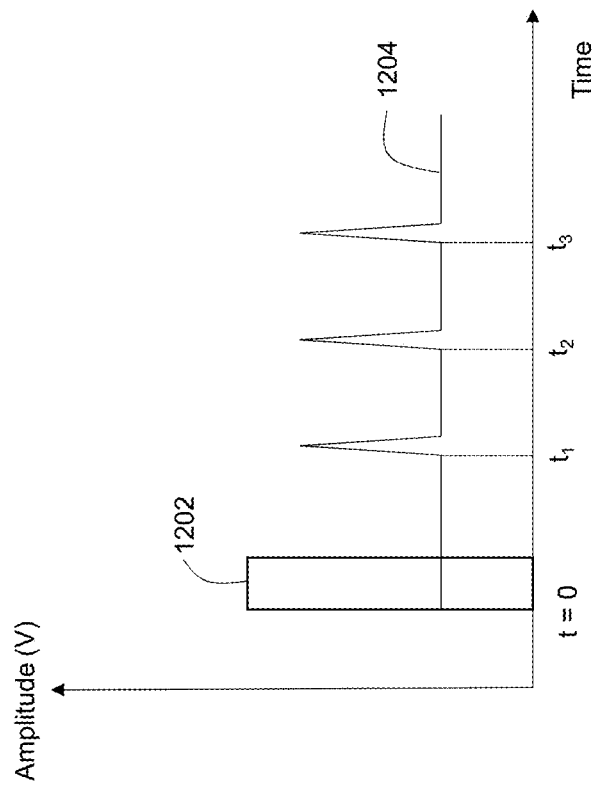
FIG. 12 is a schematic diagram showing an example timing diagram for a linear time-of-flight detector.

FIG. 12 is a schematic timing diagram that shows the relationship between the admission window 1202 that corresponds to the adjustment of the electrical potential applied to electrode 1104 by controller 114, and the measured electrical signals 1204 corresponding to secondary ions 118a. The rising edge of the admission window 1202 corresponds to time zero (t=0) for the detection cycle, and electrical signals 1204 are measured at times $t_1$, $t_2$, and $t_3$ relative to t=0.

Alternatively, in certain embodiments, ion source 102 is operated in pulsed mode by controller 114. That is, controller 114 transmits a suitable control signal to ion source 102 via signal line 120a such that ion source 102 generates a pulsed primary ion beam 116. In this mode of operation, the control signal transmitted to ion source 102 to initiate a pulse of primary ions can function as a clock signal for the ion detection cycle. That is, referring to FIG. 12, the control signal transmitted to ion source 102 to initiate a pulse primary ions also defines t=0 for purposes of detecting secondary ions 118a. In certain embodiments, when ion source 102 operates in pulsed mode, secondary ions 118a are not gated by electrode 1104 and aperture 1112 in detector 1100. Secondary ion signals measured by detection element 1106 are each time-referenced to t=0 defined by the primary ion pulse control signal transmitted by controller 114. Successive control signals transmitted to ion source 102 are sufficiently separated temporally such that an ion detection sequence is completed following each pulse of primary ions, before the next pulse of primary ions is generated.

Figure 13:
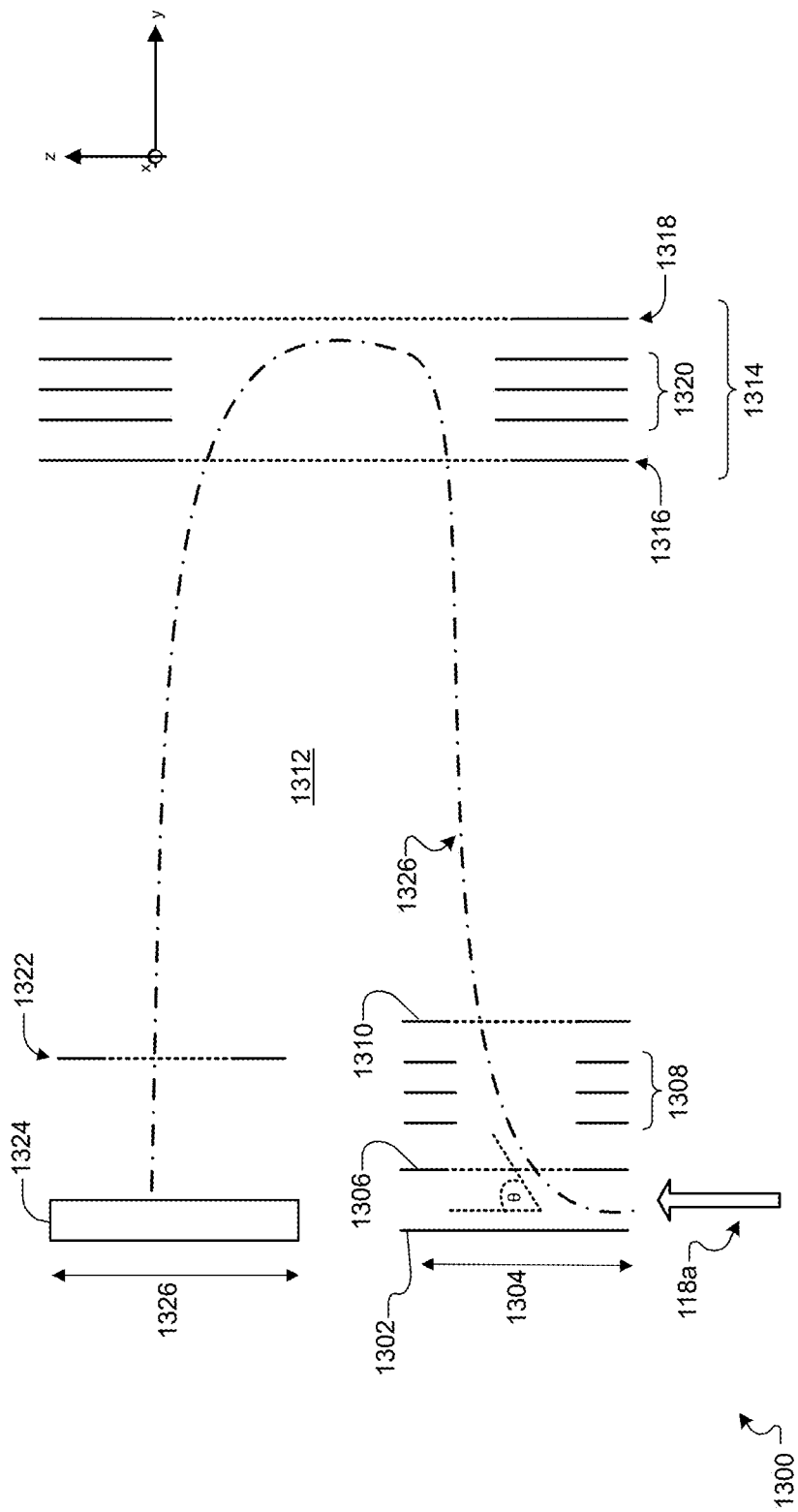
FIG. 13 is a schematic diagram showing an example of an orthogonal time-of-flight detector.

In some embodiments, detection apparatus 112 includes an orthogonal time-of-flight (ortho-TOF) detector. FIG. 13 is a schematic diagram of an ortho-TOF detector 1300. During operation, secondary ions 118a enter detector 1300 from ion optics 110 and travel along path 1326 to a detection element 1324.

Secondary ions 118a have a velocity in the z-direction when they enter detector 1300. A "push out" voltage pulse (i.e., a "gate signal") is applied by controller 114 via signal line 120f to a push out electrode 1302, and pull out voltage pulses are by applied by controller 114 via signal line 120f to grids 1306 and 1310 to accelerate a population of secondary ions 118a in the y-direction, deflecting the path of secondary ions 118a by a deflection angle θ, relative to the z-direction. Deflection angle θ, which corresponds to the angle of deflection of the secondary ions 118a from their initial propagation direction, can generally be between 60 degrees and 120 degrees (e.g., between 60 degrees and 110 degrees, between 70 degrees and 90 degrees, between 80 degrees and 90 degrees).

Electrodes 1308 are connected to controller 114 via signal line 120f. Controller 114 applies electrical potentials to electrodes 1308 to accelerate the deflected secondary ions 118a in the y-direction toward ion reflector 1314.

After passing through grid 1310, the deflected secondary ions 118a travel in a field-free space 1312 until they reach ion reflector 1314. Ion reflector 1314 includes grids 1316 and 1318 and annular electrodes 1320, each of which is connected to controller 114 via signal line 120f. Controller 114 applies suitable electrical potentials to grids 1316 and 1318 and to annular electrodes 1320 such that ion reflector functions as an "ion mirror", altering the propagation direction of secondary ions 118a along the y-direction and effectively "reflecting" the ions back through field free spatial region 1312.

The secondary ions 118a pass through grid 1322 and are incident on detection element 1324. Detection element 1324 typically has a width 1326 measured in the z-direction of between 0.5 cm and 5 cm, (e.g., between 1 cm and 3 cm). To detect all pushed out ions 118a, the width 1304 of the push out plate 1302 in the z-direction is typically within the same ranges as the width of detection element 1324, and can be similar to the width of detection element 1324.

In the ortho-TOF detector 1300, the time-of-flight of secondary ions 118a is measured in the y-direction, while the original propagation direction of secondary ions 118a upon entering detector 1300 from ion optics 110 is in the z-direction. As such, the ortho-TOF detector 1300 effectively resets the time zero for secondary ions 118a before their time of flight is measured in the detector. Whereas in the lin-TOF detector described above time zero was defined, for example, by the pulse control signal transmitted to ion source 102, in the ortho-TOF detector 1300 time zero is effectively defined by the push out signal applied to electrode 1302.

Ortho-TOF detectors can have significant advantages over lin-TOF detectors when measuring secondary ions. For example, in a lin-TOF detector used together with a pulsed ion source 102, the time zero to which measured secondary ion signals are referenced corresponds to the control signal transmitted to the ion source to generate a pulse of primary ions. Consequently, the temporal pulse width of the primary ion beam 116 is designed to be relatively short (e.g., approximately 10 ns) to accurately measure only ions that are generated from the sample in response to that pulse of primary ions. Further, because the control signal transmitted to the ion source establishes time zero for the entire ion detection cycle, the control signal is typically much shorter than the ion detection cycle to ensure that the uncertainty in mass resolution (which depends on time zero) is sufficiently low. That is, for the uncertainty in mass resolution to be acceptably small, the temporal width of the control signal is significantly shorter than the ion detection cycle.

In contrast, because the pulse width of the primary ion beam 116 does not establish time zero for an ortho-TOF detector, the pulse width of the primary ion beam can be significantly larger (e.g., 3 μs). As a result, a much greater population of secondary ions 118a is produced from the sample, which in turn leads to much larger measured ion signals.

Further, while nearly all of the secondary ions 118a generated from the sample can be measured by a lin-TOF detector (effectively no losses due to duty cycle), completion of a detection cycle takes a comparatively longer time than the temporal width of the pulses of primary ions that generate the secondary ions 118a. Thus, for example, a typical detection cycle may be completed in approximately 20 microseconds, for secondary electrons generated in response to a 10 ns primary ion pulse. As a result, for every 10 ns of sample ionization, 20 microseconds are consumed by detecting secondary ion signals. Put another way, for every 1 second of analysis time, secondary ions are only generated for approximately 500 microseconds. This can severely limit the throughput of the system, and can be a significant problem when large samples and/or scanning areas are involved.

As described above in connection with lin-TOF detectors, an ortho-TOF detector can be used in system 100 with ion source 102 continuously generating primary ion beam 116. When primary ions are continuously generated, secondary ions 118a are also continuously generated from sample 150, and enter ortho-TOF detector 1300 in the vicinity of push out electrode 1302.

Ortho-TOF detector 1300, however, operates in pulsed mode, with controller 114 applying push out signals to push out electrode 1302 at a particular repetition rate. In some embodiments, for example, the repetition rate is approximately 100 kHz, although detector 1300 can generally operate at a wide variety of different repetition rates. In general, the repetition rate of the push out signals is selected to allow sufficient time for measurement of signals due to the secondary ions 118a admitted into detector 1300.

Further, the temporal width of the push out signals applied to push out electrode 1302 by controller 114 is selected to ensure that the push out region of detector 1300 is filled with secondary ions 118a. After the push out region of detector 1300 is filled, however, space-charge effects and ion scattering events can adversely affect precise establishment of time zero. In certain embodiments, for example, the temporal width of the push out signals applied by controller 114 to push out electrode 1302 is approximately 3 microseconds, although in general, a wide variety of different push out signal widths can be used.

In summary, both the repetition rate and temporal pulse width of the push out signals applied by controller 114 to push out electrode 1302 are selected to ensure that secondary ion signals are accurately and reproducibly measured by the detector. However, when secondary ions 118a are continuously generated by a primary ion beam 116 that is continuously produced by ion source 102, a relatively modest fraction of the total population of secondary ions 118a generated are detected by the ortho-TOF detector. For example, an ortho-TOF operating at a 100 kHz repetition rate with 3 microsecond push out signals may only measure approximately 30% of the total population of secondary ions 118a that are generated from the sample.

The relatively low proportion of secondary ions 118a that are measured can have several undesirable consequences. First, by only measuring a relatively small fraction of the total population of secondary ions 118a that are generated, the measured secondary ion signals are significantly weaker than they would otherwise be if a larger fraction of the total secondary ion population was detected. As a result, the measurement sensitivity of system 100 is lower than it would be if a larger fraction of the secondary ions were detected. As an example, by detecting only about 30% of the secondary ions that are generated, the measurement sensitivity of system 100 can be reduced by a factor of 3-4.

Secondary ions 118a that are not deflected along path 1326 within detector 1300 simply scatter within the detector. Thus, for example, if the period of the detector's duty cycle is 10 microseconds and secondary ions 118a are deflected along path 1326 for only 3 microseconds of the duty cycle period, then for the remaining 7 microseconds, secondary ions 118a that enter detector 1300 simply scatter away within the detector. Some of these scattered ions, however, can still reach detection element 1324 and generate spurious background signals. Such background signals effectively function as noise within detector 1300, making discrimination of TOF-based secondary ion signals more difficult. Accordingly, in addition to reducing the sensitivity of system 100 by selectively detecting a relatively small fraction of secondary ions 118a, the scattering of undetected secondary ions can also lead to increased baseline noise, against which secondary ion signals are measured.

Further, by generating a relatively large fraction of secondary ions 118a that are not detected, a relatively significant signal-generating portion of the sample is "wasted". As the primary ion beam 116 is scanned over the sample and secondary ions 118a are generated, the sample is ablated by primary ion beam 116. As such, each sample is capable of generating only a finite number of secondary ions 118a before the sample is consumed. By discarding a significant proportion of the generated secondary ions 118a, much of the sample is effectively wasted during the measurements.

To improve the match between the population of secondary ions 118a generated from the sample and the capacity of the push out region within detector 1300, and to better utilize the sample to generate secondary ions 118a that are actually detected, ion source 102 can be operated in a pulsed mode. Controller 114 transmits a control signal via signal line 120a to cause ion source 102 to generate a pulsed primary ion beam 116. Typically, the control signal is periodic and includes a sequence of trigger or gate pulses having a selected temporal width, at a selected repetition rate. Each trigger or gate pulse causes ion source 102 to generate a pulse of primary ions. Accordingly, the pulsed primary ion beam 116 has a repetition rate that is the same as the repetition rate of the control signal transmitted by controller 114.

Operating ion source 102 in pulsed mode can also be advantageous because the average primary ion current of ion source 102 can be maintained at the same level as in continuous mode operation, but because the source is pulsed, the instantaneous primary ion current per pulse is increased. Accordingly, sample erosion due to exposure to primary ion beam 116 occurs at the same rate, but the measurement sensitivity of system 100 increases since a larger fraction of secondary ions liberated from the sample are measured.

In general, controller 114 can adjust both the repetition rate and the temporal pulse width of the control signal transmitted to ion source 102. In particular, each of these parameters can be adjusted to increase the fraction of the generated secondary ion population that is measured by detector 1300.

In some embodiments, for example, the temporal pulse width of the control signal transmitted to ion source 102 can be adjusted based on an ion capacity of the push out region of detector 1300. The push out region of detector 1300 corresponds to the spatial region between push out electrode 1302 and grid 1306. Due to space-charge effects, collision events, and geometrical constraints, the push out region has a finite storage capacity $N_{fill}$ for secondary ions 118a. Based on the average ion transport rate $v_{ion}$ within system 100, from the time at which secondary ions 118a are first generated by primary ion beam 116, the push out region (which initially contains no secondary ions) is filled with $N_{fill}$ ions within a time period $t_{fill}$, which corresponds approximately to $t_{fill} = N_{fill}/v_{ion}$. To increase the fraction of the secondary ion population that is measured by detector 1300, controller 114 can adjust the temporal width of the pulses in the control signal transmitted to ion source 102 to match the time period $t_{fill}$ required to fill the push out region of detector 1300 with secondary ions. In certain embodiments, for example, a difference between the temporal width of the pulses of the control signal transmitted to ion source 102 and the time period $t_{fill}$ required to fill the push out region of detector 1300 with secondary ions is 10% or less (e.g., 8% or less, 5% or less, 4% or less, 3% or less, 2% or less, 1% or less) of the time period $t_{fill}$.

After the push out region of detector 1300 is filled with secondary ions 118a, controller 114 applies a push out signal to push out electrode 1302 to deflect secondary ions 118a along path 1326 in detector 1300. As discussed above, the push out signal is a periodic signal that consists of repeating pulses having an amplitude and a temporal width.

The temporal widths of the pulses in the control signal transmitted to ion source 102 effectively define the temporal widths of the pulses of primary ions in primary ion beam 116. Further, because each primary ion pulse generates a population of secondary ions 118a, the temporal widths of the pulses in the control signal transmitted to ion source 102 also effectively define the temporal widths of pulses of secondary ions 118a that are generated from the sample in response to a pulsed primary ion beam.

Matching the temporal width of the pulses in the control signal transmitted to ion source 102 to the time period $t_{fill}$ for filling the push out region of detector 1300 with secondary ions 118a can ensure that the ion capacity of detector 1300 is more fully utilized, and therefore the secondary ion signals measured by detection element 1324 are of larger amplitude than they would otherwise be if the push out region of detector 1300 was filled with fewer secondary ions.

In certain embodiments, controller 114 can adjust the repetition rate of the control signal transmitted to ion source 102 (i.e., the repetition rate of pulsed primary ion beam 116) based on the repetition rate of the push out signal applied by controller 114 to push out electrode 1302. In particular, by ensuring that the repetition rate of the control signal transmitted to ion source 102 matches the repetition rate of the push out signal applied by controller 114 to push out electrode 1302, a significantly larger fraction of the secondary ions 118a generated from the sample can be deflected within detector 1300 and measured. Because the repetition rate of the push out signal is selected by controller 114 based on the analysis time for a complete ion detection cycle, matching the repetition rates ensures that each pulse or packet of secondary ions 118a that arrives at detector 1300 is deflected and analyzed and, just as the ion detection cycle is complete, another pulse or packet of secondary ions 118a arrives for analysis.

In this manner, matching the repetition rates of the control signal applied to ion source 102 and the push out signal applied to push out electrode 1302 ensures that a higher proportion of generated secondary ions are measured, which leads to a number of advantages. Namely, as discussed above, a significantly higher fraction of the sample is consumed in the generation of secondary ions 118a that are actually measured, rather than secondary ions that are merely discarded during the ion detection cycle. In addition, background noise in detector 1300 is reduced, because contributions from discarded secondary ions 118a are significantly reduced. In some embodiments, the repetition rate of the pulses in the control signal transmitted to ion source 102 and the repetition rate of the pulses in the push out signal applied to push out electrode 1302 differ by 10% or less (e.g., 8% or less, 5% or less, 4% or less, 3% or less, 2% or less, 1% or less) of the repetition rate of the pulses in the push out signal.

The repetition rate of the pulses in the control signal transmitted to ion source 102 effectively define both the repetition rate of primary ion pulses in primary ion beam 116 and the repetition rate of pulses of secondary ions 118a liberated from the sample in response to the pulses of primary ions. Accordingly, in certain embodiments, the repetition rate of primary ion pulses in primary ion beam 116 and the repetition rate of the pulses in the push out signal applied to push out electrode 1302 differ by 10% or less (e.g., 8% or less, 5% or less, 4% or less, 3% or less, 2% or less, 1% or less) of the repetition rate of the pulses in the push out signal. Further, the repetition rate of pulses of secondary ions liberated from the sample and the repetition rate of the pulses in the push out signal applied to push out electrode 1302 differ by 10% or less (e.g., 8% or less, 5% or less, 4% or less, 3% or less, 2% or less, 1% or less) of the repetition rate of the pulses in the push out signal.

The process of generating pulses of primary ions and transporting the primary ion pulses to the sample to generate secondary ions 118a occurs over a non-zero time period. Further, once generated from the sample, secondary ions 118a propagate from chamber 126 through ion optics 110 to reach detection apparatus 112 over an additional non-zero time period. To further increase the fraction of secondary ions 118a that are deflected and measured within detector 1300, controller 114 can account for the average delay period between transmission of the control signal to ion source 102 and the arrival of secondary ion pulses or packets at detector 1300 by introducing a temporal offset (i.e., a phase offset) between the control signal transmitted to ion source 102 and the push out signal applied to push out electrode 1302. The magnitude of the temporal offset is selected to ensure that the push out signal is applied to push out electrode 1302 just as the push out region of detector 1300 fills with secondary ions 118*a*. This ensures that as many secondary ions as possible are deflected into detector 1300 for analysis.

In practice, controller 114 can select a temporal offset of suitable magnitude by generating pulses or packets of secondary ions 118*a* from a test sample, and iteratively adjusting the temporal offset between the two signals until secondary ion signals of sufficient amplitude are measured by detector 1300. As the magnitude of the temporal offset more closely approaches the delay period between transmission of the control signal to ion source 102 and the filling time of the push out region in detector 1300, the measured amplitudes of the secondary ion signals are expected to increase.

The foregoing operations of matching the repetition rate of the control signal transmitted to ion source 102 to the push out signal applied to push out electrode 1302 and, optionally, adjusting a temporal offset between the signals, yields a control signal transmitted to ion source 102 (which produces a pulsed primary ion beam 116 having a repetition rate) that is synchronized to the push out signal applied to push out electrode 1302. While synchronization and pulse width adjustment are used in the methods and systems discussed herein to significantly improved the sensitivity of system 100 and reduce baseline noise, such steps have generally not been implemented in conventional mass spectral analysis of biological samples, in part because conventional methods typically lack fine control over the timing of ion generation from a sample.

Many biological samples are analyzed, for example, using methods such as electrospray ionization. In such methods, precise establishment of time zero is difficult or even impossible. Electrospray ionization is typically performed continuously rather than in a pulsed manner. Moreover, even if performed in a pulsed manner, the ionization process is dependent upon analyte flow rates and other solution transport parameters. Accordingly, it is in many circumstances not possible to generate packets or pulses of ions at a precise repetition rate. As a result, adjustment of pulse widths and the repetition rates (and temporal offsets) of control signals, as discussed above, has generally not been used in connection with the analysis of biological samples.

As discussed above, synchronization of the push out signal applied to push out electrode 1302 and the control signal transmitted to ion source 102 (and to the resulting repetition rate of pulsed primary ion beam 116) can increase the fraction of secondary ions 118*a* generated from sample 150 that are detected by detector 1300. Synchronization can lead to a substantial fraction of the generated secondary ions 118*a* (e.g., more than 50%, more than 60%, more than 70%, more than 80%, more than 90%, more than 95%, more than 98%, or even more) being measured by detector 1300.

Figure 14:
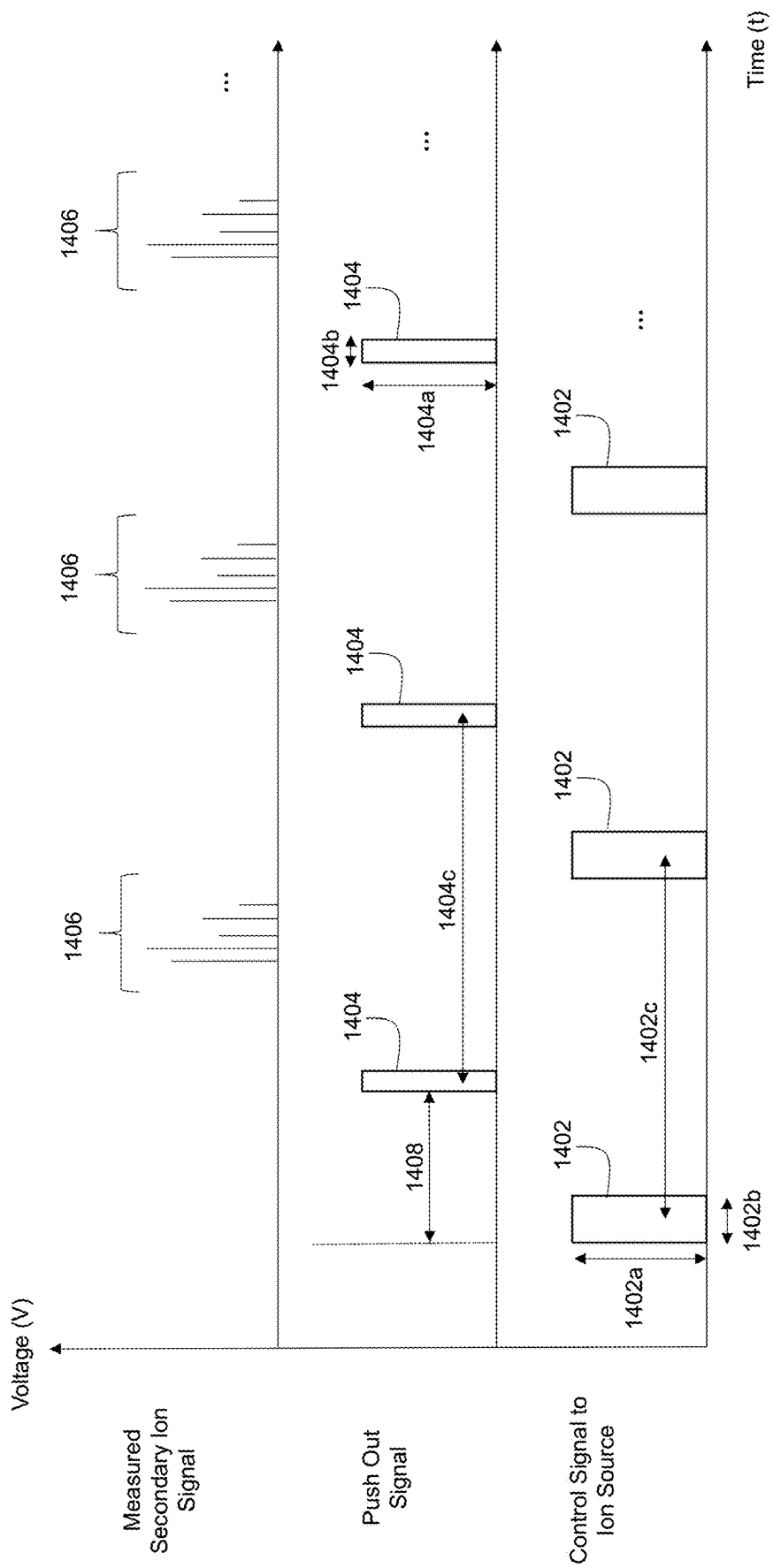
FIG. 14 is a schematic diagram showing an example timing diagram for an orthogonal time-of-flight detector.

FIG. 14 is a schematic timing diagram showing examples of control signals transmitted by controller 114 and measurement signals obtained by detector 1300. Controller 114 transmits a control signal consisting of a periodic sequence of voltage pulses 1402 to ion source 102 to cause ion source 102 to produce primary ion beam 116 consisting of a sequence of pulses of primary ions. The primary ion pulses interact with sample 150, generating pulses or packets of secondary ions 118*a*, which propagate to detection apparatus 112 (e.g., detector 1300).

Controller 114 applies a push out signal consisting of a periodic sequence of voltage pulses 1404 to push out electrode 1302, deflecting and accelerating secondary ions 118*a* in the push out region of detector 1300 in the y-direction. When the secondary ions reach detection element 1324, the detection element measures the secondary ions as a function of arrival time relative to time zero (to) established by each corresponding pulse in the push out signal, as discussed above. The measured secondary ion signals 1406 correspond to ion abundance measurements as a function of m/z for the secondary ions 118*a*, since the time-of-flight of a secondary ion 118*a* in detector 1300 (i.e., along path 1326) is related to the ion's mass-to-charge ratio.

Each of the pulses 1402 in the control signal transmitted to ion source 102 has an amplitude 1402*a* and a temporal duration (or "width") 1402*b*. The sequence of pulses 1402 has a temporal period 1402*c* that defines a frequency of the pulse sequence. Each of the pulses 1404 in the push out signal applied to push out electrode 1302 has an amplitude 1404*a*, a temporal duration (or "width") 1404*b*, and a temporal period 1404*c* that defines a frequency of the pulses in the sequence.

As discussed above, the temporal width 1402*b* of pulses 1402 can be approximately matched to the filling time $t_{fill}$ for the push out region of detector 1300 to ensure that the population of secondary ions 118*a* generated from the sample from each incident primary ion pulse is approximately sufficient to just fill the push out region of detector 1300. In certain embodiments, for example, temporal width 1402 can be between 5 nanoseconds and 100 microseconds (e.g., between 50 nanoseconds and 80 microseconds, between 100 nanoseconds and 50 microseconds, between 500 nanoseconds and 50 microseconds, between 1 microsecond and 50 microseconds, between 1 microsecond and 30 microseconds, between 1 microsecond and 20 microseconds, between 1 microsecond and 10 microseconds, between 2 microseconds and 10 microseconds, between 2 microseconds and 8 microseconds, between 3 microseconds and 5 microseconds).

Because the temporal width of 1402*b* of pulses 1402 effectively determines the temporal width of pulses of primary ions in primary ion beam 116, the temporal pulse width of primary ion beam 116 can be between 5 nanoseconds and 100 microseconds (e.g., between 50 nanoseconds and 80 microseconds, between 100 nanoseconds and 50 microseconds, between 500 nanoseconds and 50 microseconds, between 1 microsecond and 50 microseconds, between 1 microsecond and 30 microseconds, between 1 microsecond and 20 microseconds, between 1 microsecond and 10 microseconds, between 2 microseconds and 10 microseconds, between 2 microseconds and 8 microseconds, between 3 microseconds and 5 microseconds).

The temporal width 1404*b* of pulses 1404 can be selected as desired to ensure that secondary ions 118*a* are deflected and accelerated within detector 1300. For example, in some embodiments, temporal width 1404*b* can be between 5 nanoseconds and 100 microseconds (e.g., 50 nanoseconds and 100 microseconds, between 100 nanoseconds and 100 microseconds, between 500 nanoseconds and 100 microseconds, between 700 nanoseconds and 100 microseconds, between 1 microsecond and 80 microseconds, between 1 microsecond and 50 microseconds, between 2 microseconds and 50 microseconds, between 10 microseconds and 50 microseconds, between 3 microseconds and 30 microseconds, between 3 microseconds and 20 microseconds).

In general, the amplitudes 1402*a* and 1404*a* of pulses 1402 and 1404 can be selected as desired to implement suitable control functions. In some embodiments, for example, pulse amplitude 1402*a* can be between 1000 V and 5000 V. In certain embodiments, pulse amplitude 1404*a* can be between 100 V and 3000 V.

As described above, the temporal periods 1402c and 1404c of the sequences of pulses 1402 and 1404 are approximately matched to ensure that each pulse or packet of secondary electrons 118a that is generated from the sample arrives at detection apparatus 112 (e.g., detector 1300) after the conclusion of a prior ion detection cycle. As a result, all of the secondary ions in each arriving secondary ion pulse or packet can be deflected into and measured by detector 1300; few, if any, of the secondary ions are scattered or otherwise rejected.

The durations of the temporal periods 1402c and 1404c are selected by controller 114 based on the time elapsed during each ion detection cycle. The elapsed time depends on the length of the flight path within detector 1300, the voltages applied to accelerate the secondary ions, the m/z of the secondary ions, and the speed of various hardware and software components of detector 1300. In some embodiments, for example, temporal periods 1402c and 1404c are each between 5 microseconds and 50 microseconds (e.g., between 10 microseconds and 40 microseconds, between 15 microseconds and 30 microseconds).

In connection with temporal periods 1402c and 1404c, in some embodiments, frequencies (or repetition rates) of the control signal transmitted to ion source 102 (i.e., pulses 1402) and the push out signal applied to push out electrode 1302 (i.e., pulses 1404) are each between 1 kHz and 200 kHz (e.g., between 10 kHz and 100 kHz, between 80 kHz and 100 kHz). Because pulses 1402 transmitted to ion source 102 each generate pulses of primary ions that form primary ion beam 116, the repetition rate of pulsed primary ion beam 116 can also be between 1 kHz and 200 kHz (e.g., between 10 kHz and 100 kHz, between 80 kHz and 100 kHz).

As discussed above the temporal offset (or phase offset) 1408 between pulses 1402 and 1404 reflects the non-zero delay period between the transmission of the control signal to ion source 102 by controller 114 and the arrival of corresponding pulses or packets of secondary ions 118a at detection apparatus 112. Controller 114 is generally configured to adjust the temporal offset value 1408 to control the amplitude s of secondary ion signals that are measured. The magnitude of the delay period, and therefore the magnitude of temporal offset 1408, depends upon a number of factors, including the length of path 1326, the m/z of the secondary ions that are measured, and various accelerating, decelerating, focusing, and deflecting fields through which the primary and secondary ions pass. In some embodiments, for example, the magnitude of temporal offset 1408 can be 80% or less (e.g., 70% or less, 60% or less, 50% or less, 40% or less, 30% or less, 25% or less, 20% or less, 15% or less, 10% or less, 5% or less, or even less) of temporal periods 1402c and 1404c.

It should be noted that as a pulse or packet of secondary ions 118a propagates from sample 150 to detection apparatus 112, the spatial distribution of secondary ions within the pulse can broaden due to the different m/z values among the ions. By adjusting the temporal width 1402b of pulses 1402 in the control signal transmitted to ion source 102, variations in the time $t_{fill}$ required to fill the push out region of detector 1300 can be accounted for.

In some embodiments, due to spatiotemporal broadening of the pulses of secondary ions 118a liberated from the sample as they propagate through system 100, not all secondary ions 118a arrive in the push out region of detector 1300 within the temporal width 1404b of the pulses of the push out signal. In such circumstances, the temporal offset 1408 can be adjusted to take advantage of this spatiotemporal broadening to selectively deflect and detect secondary ions with a specific subset of m/z values within detector 1300. Because the secondary ion arrival times within the push out region will depend on their m/z values, by adjusting the temporal offset 1408 such that push out signal pulses are applied to push out electrode 1302 when secondary ions with a particular subset of m/z values are present within the push out region, measurement and analysis of secondary ions by detector 1300 can be effectively restricted to that subset of m/z values. As an example, in some embodiments, secondary ions 118a corresponding to relatively heavier masses (e.g., secondary ions derived from lanthanide element-based mass tags) can be selectively measured by detector 1300 by adjusting the temporal offset 1408. In certain embodiments, secondary ions 118a corresponding to lighter masses (e.g., secondary ions derived from atoms such as sodium and potassium) can be selectively measured by detector 1300 by adjusting the temporal offset 1408 to a different value. By preferentially selecting relatively heavier masses for measurement, the average mass of the secondary ions that are not measured is less than the average mass of the secondary ions that are measured. In contrast, by preferentially selecting relatively lighter masses for measurement, the average mass of the secondary ions that are not measured is greater than the average mass of the secondary ions that are measured.

Figure 15:
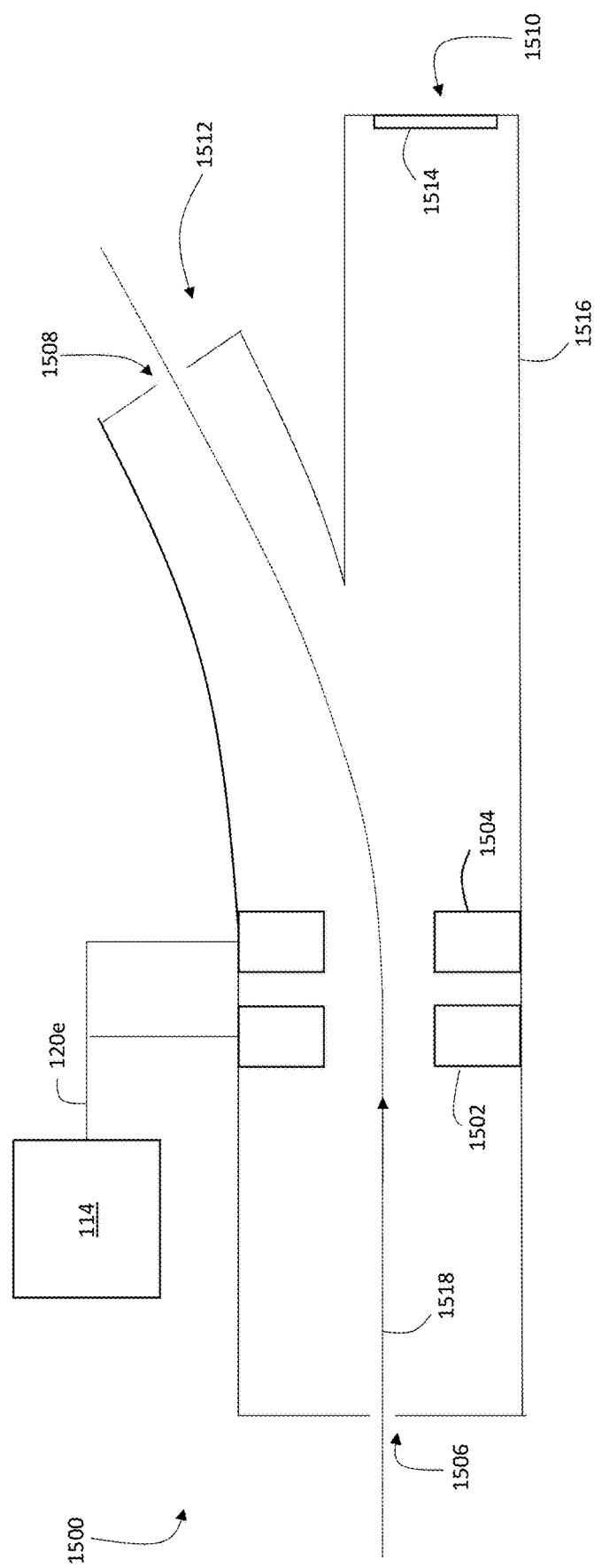
FIG. 15 is a schematic diagram showing an example of an electrostatic flapper valve.

Other mechanisms and steps can also be used to effectively filter secondary ions 118a such that only ions with m/z values within a particular range are measured by detection apparatus 112. In certain embodiments, ion optics 110 can include a "flapper" valve that preferentially directs secondary ions into detection apparatus 112 (e.g., detector 1300). FIG. 15 is a schematic diagram showing an embodiment of a flapper valve 1500. Valve 1500 includes a housing 1516 that includes an entrance aperture 1506 and two ports 1510 and 1512. A blocking element 1514 is positioned at the end of port 1510, and an exit aperture 1508 is positioned at the end of port 1512. Deflection electrodes 1502 and 1504 are positioned within housing 1516 and connected to controller 114 via signal line 120e.

During operation, a pulse or packet of secondary ions 118a enters valve 1500 through entrance aperture 1506. As discussed above, during propagation through system 100, spatiotemporal dispersal of the secondary ion pulse leads to a spatial dispersal of secondary ions within the pulse, with ions of smaller m/z leading ions of larger m/z. Valve 1500 can be used to preferentially direct a subset of secondary ions—corresponding to a selected range of m/z values—to emerge from aperture 1508 by applying suitable electrical potentials to electrodes 1502 and/or 1504. When no potentials are applied to electrodes 1502 and/or 1504, secondary ions 118a pass through the electrodes undeflected, and are intercepted by blocking member 1514, preventing them from reaching detection apparatus 112. However, when suitable potentials are applied to electrodes 1502 and/or 1504, secondary ions 118a are deflected along path 1518, emerging from aperture 1508 and entering detection apparatus 112. By applying suitable electrical potentials to electrodes 1502 and/or 1504 during a particular time window as secondary ions 118a pass through valve 1500, controller 114 can selectively direct a subset of the secondary ions corresponding to a particular range of m/z values to detection apparatus 112 for analysis.

In addition to valve 1500, other mechanisms and devices can also be used to selectively introduce a subset of the liberated secondary ions 118a—corresponding to a particular range of m/z values—into detection apparatus 112 for measurement. Such devices include, but are not limited to, a variety of adjustable mechanical blocking members and electrode assemblies. Where such mechanisms (such as valve 1500) include electrodes to which controller 114 delivers control signals to selectively deflect secondary ions 118*a*, the control signals can by synchronized (with an appropriate temporal offset) to the control signal transmitted to ion source 102 and to the push out signal applied to push out electrode 1302 to ensure that approximately the same subset of m/z ratios is selected for analysis from each pulse of secondary ions 118*a*. In addition, the temporal width of the control signal delivered to such mechanisms (e.g., the electrical potentials applied to electrodes 1502 and/or 1504) can be adjusted to select the width of the distribution of m/z values that are analyzed.

Valve 1500 can be particularly useful for selectively analyzing certain types of secondary ions that provide different types of information. For example, many relatively light secondary ions, such as sodium and potassium ions, can be detected by detection apparatus 112 to provide images of the general structure (e.g., tissue structure) of a sample. Because these ions are typically widely distributed throughout samples, they yield relatively strong measurement signals, and therefore provide bright, detailed, and non-selective sample images.

In contrast, secondary ions derived from mass tags typically provide information about localized distributions of particular sample components such as proteins. As such, images derived from these types of secondary ions may be of relatively low intensity in some corresponding regions of the sample, depending upon the distribution of specific sample components in various sample regions.

By selectively admitting only secondary ions with certain ranges of m/z values to detection apparatus 112 for analysis, both types of information can be obtained. For example, in some embodiments, valve 1500 (or another mechanism) can be operated by controller 114 to first acquire one or more images of sample 150 by detecting only relatively light secondary ions of elements such as sodium and/or potassium. These images provide an "overview" or general picture of the sample. Then valve 1500 (or another mechanism) can be operated by controller 114 to acquire one or more images of sample 150 by detecting secondary ions derived from mass tags. These images provide structure-specific information about the location, distribution, and quantities of various sample components.

In certain embodiments, controller 114 is configured to obtain both types of images in sequence by selectively detecting different types of secondary ions using valve 1500 or another mechanism. For example, controller 114 can be configured to operate valve 1500 such that for each set of (n−1) images of sample 150 that are obtained by detecting secondary ions derived from mass tags, a survey image of sample 150 obtained by selectively detecting relatively light secondary ions (e.g., Na, K) from sample 150 is obtained. The survey image can be acquired either before or after the (n−1) structure-specific images, and can be used, for example, to select exposure parameters and an exposure pattern for the sample.

Mechanisms such as valve 1500 can be used together with the other methods and system components discussed above to further improve the precision and accuracy of measurements performed using system 100. In particular, by filtering out and preventing secondary ions 118*a* that are not of interest from reaching detection apparatus 112, baseline signal noise can be reduced, allowing weaker signals from secondary ions of interest to be discriminated against the baseline signal.

OTHER EMBODIMENTS

While this specification contains many specific implementation details, these should not be construed as limitations on the scope of the disclosure or on the scope of what may be claimed, but rather as descriptions of features that may be specific to particular embodiments. Features that are described in this specification in the context of separate embodiments can also be implemented in combination in a single embodiment unless expressly stated otherwise. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims.

What is claimed is:

1. A method comprising:
   directing an ion beam to a region of a sample to liberate charged particles from the region of the sample, wherein the directed ion beam is pulsed at a first repetition rate;
   deflecting a first subset of the liberated charged particles from a first path to a second path different from the first path in response to a gate signal synchronized with the repetition rate of the pulsed ion beam; and
   detecting the first subset of the liberated charged particles in a time-of-flight (TOF) mass spectrometer to determine information about the sample, wherein the gate signal sets a common reference time for the TOF mass spectrometer for the first subset of charged particles liberated by each pulse of the ion beam.

2. The method of claim 1, wherein TOF mass spectrometer differentiates mass-to-charge ratio differences among the first subset of charged particles based on differences in detection time for their time-of-flight relative to the common reference time.

3. The method of claim 1, wherein the gate signal is synchronized with the repetition rate of the pulsed ion beam to cause the first subset to comprise a substantial portion of at least one type of the liberated charged particles propagating along the first path.

4. The method of claim 3, wherein the substantial portion comprises more than 50%.

5. The method of claim 1, wherein the directed ion beam has a pulse width of between 5 nanoseconds and 100 microseconds.

6. The method of claim 5, wherein the directed ion beam has a pulse width of between 100 nanoseconds and 50 microseconds.

7. The method of claim 1, wherein the first repetition rate is between 1 kHz and 200 kHz.

8. The method of claim 1, wherein the first subset of the liberated charged particles are deflected at an angle of between 60 degrees and 120 degrees from the first path to the second path.

9. The method of claim 1, wherein the gate signal comprises a voltage pulse applied to an ion optic electrode to cause the deflection.

10. The method of claim 9, wherein the liberated charged particles travel along the first path at different speeds depending on their masses, and wherein a delay between the voltage pulse and the pulsed ion beam is set to select a certain range of charged particle masses to be in the first subset from among the liberated charged particles.

11. The method of claim 10, wherein the delay between the voltage pulse and the pulsed ion beam is set so that heavier masses from among the liberated charged particles are selected in the first subset of charged particles.

12. The method of claim 1, further comprising blocking a second subset of the liberated charged particles propagating along the first path from entering a chamber containing the TOF mass spectrometer.

13. The method of claim 12, wherein the blocking of the second subset occurs during a time period different from the deflecting and is also synchronized with the repetition rate of the pulsed ion beam.

14. The method of claim 1, wherein the liberated charged particles comprise secondary elemental atomic ions derived from mass tags associated with the sample, and wherein the pulsed ion beam liberates the charged particles by ionizing the mass tags.

15. The method of claim 14, wherein the sample is a planar sample comprising biological material on a conductive substrate.

16. The method of claim 1, further comprising scanning the pulsed ion beam relative to the sample to irradiate additional regions of the sample, and further performing the deflecting and the detecting for each of the additional regions of the sample.

17. A mass spectroscopy system comprising:
a pulsed ion source configured to direct an ion beam to a region of a sample to liberate charged particles from the region of the sample, wherein the pulsed ion source generates pulses of the ion beam at a first repetition rate;
ion optics controllable to adjustably deflect a first subset of the liberated charged particles from a first path to a second path different from the first path;
an ion optic controller coupled to the pulsed ion source and configured to generate a gate signal synchronized with the repetition rate of the pulsed ion beam to cause the ion optics to deflect the first subset from the first path to the second path; and
a time-of-flight (TOF) mass spectrometer positioned to detect the first subset of the liberated charged particles to determine information about the sample, wherein the gate signal sets a common reference time for the TOF mass spectrometer for the first subset of charged particles liberated by each pulse of the ion beam.

18. The system of claim 17, wherein the TOF mass spectrometer is configured to differentiate mass-to-charge ratio differences among the first subset of charged particles based on differences in detection time for their time-of-flight relative to the common reference time.

19. The system of claim 17, wherein the gate signal is synchronized with the repetition rate of the pulsed ion beam to cause the first subset to comprise a substantial portion of at least one type of the liberated charged particles propagating along the first path.

20. The system of claim 19, wherein the substantial portion comprises more than 50%.

21. The system of claim 17, wherein the directed ion beam has a pulse width of between 5 nanoseconds and 100 microseconds.

22. The system of claim 17, wherein the first repetition rate is between 1 kHz and 200 kHz.

23. The system of claim 17, wherein the gate signal comprises a voltage pulse, and wherein the ion optic controller is configured to apply the gate signal to an ion optic electrode to cause the deflection.

24. The system of claim 23, wherein the voltage pulse has a pulse width of between 500 nanoseconds and 50 microseconds.

25. The system of claim 23, wherein the liberated charged particles travel along the first path at different speeds depending on their masses, and wherein the ion optic controller is configured to set a delay between the voltage pulse and the pulsed ion beam to select a certain range of charged particle masses to be in the first subset from among the liberated charged particles.

26. The system of claim 25, wherein the ion optic controller is configured to set the delay between the voltage pulse and the pulsed ion beam so that heavier masses from among the liberated charged particles are selected in the first subset of charged particles.

27. The system of claim 17, further comprising a blocking member positioned to block a second subset of the liberated charged particles propagating along the first path from entering a chamber containing the TOF mass spectrometer, wherein the ion optic controller is configured to generate one or more electromagnetic fields using ion optic electrodes to direct the second subset of the liberated charged particles to be incident on the blocking member.

28. The system of claim 27, wherein the blocking of the second subset occurs during a time period different from the deflecting and is also synchronized with the repetition rate of the pulsed ion beam.

29. The system of claim 17, wherein the liberated charged particles comprise secondary elemental atomic ions derived from mass tags associated with the sample, and wherein the pulsed ion beam liberates the charged particles by ionizing the mass tags.

30. The system of claim 17, wherein:
the ion optic controller is configured to:
generate one or more control signals that cause the pulsed ion source to scan the pulsed ion beam relative to the sample to irradiate additional regions of the sample; and
generate one or more control signals that cause the ion optics to adjustably deflect a first subset of liberated charged particles corresponding to each additional region from a first path to a second path different from the first path; and
wherein the TOF mass spectrometer is configured to detect the first subset of the liberated charged particles corresponding to each additional region.

* * * * *